(12) United States Patent
Van Dam et al.

(10) Patent No.: US 10,473,668 B2
(45) Date of Patent: Nov. 12, 2019

(54) SELF-SHIELDED, BENCHTOP RADIO CHEMISTRY SYSTEM WITH A PLURALITY SHIELDED CARRIERS CONTAINING A DISPOSABLE CHIP CASSETTE

(71) Applicants: THE REGENTS OF THE UNIVERSITY OF CALIFORNIA, Oakland, CA (US); SOFIE BIOSCIENCES, INC., Culver City, CA (US)

(72) Inventors: R. Michael Van Dam, Los Angeles, CA (US); Melissa Moore, Culver City, CA (US); Brandon Maraglia, Culver City, CA (US); Daniel Thompson, Culver City, CA (US)

(73) Assignees: THE REGENTS OF THE UNIVERSITY OF CALIFORNIA, Oakland, CA (US); SOFIE BIOSCIENCES, INC., Culver City, CA (US)

( * ) Notice: Subject to any disclaimer, the term of this patent is extended or adjusted under 35 U.S.C. 154(b) by 0 days.

(21) Appl. No.: 15/315,369
(22) PCT Filed: Jun. 5, 2015
(86) PCT No.: PCT/US2015/034583
§ 371 (c)(1),
(2) Date: Nov. 30, 2016
(87) PCT Pub. No.: WO2015/188165
PCT Pub. Date: Dec. 10, 2015

(65) Prior Publication Data
US 2017/0102391 A1    Apr. 13, 2017

Related U.S. Application Data

(60) Provisional application No. 62/008,997, filed on Jun. 6, 2014.

(51) Int. Cl.
*G01N 33/60* (2006.01)
*A61B 6/03* (2006.01)
(Continued)

(52) U.S. Cl.
CPC .............. *G01N 33/60* (2013.01); *A61B 6/037* (2013.01); *A61B 6/48* (2013.01); *A61B 6/542* (2013.01);
(Continued)

(58) Field of Classification Search
CPC ...................................................... G01N 33/60
(Continued)

(56) References Cited

U.S. PATENT DOCUMENTS 5,759,513 A    6/1998  Nakazawa
5,972,711 A    10/1999 Barclay et al.
(Continued)

FOREIGN PATENT DOCUMENTS

EP    0510487    10/1992
EP    2562150    * 2/2013
(Continued)

OTHER PUBLICATIONS

Yang, H. et al, Analytical Chemistry 2009, 81, 1061-1067.*
(Continued)

*Primary Examiner* — Arlen Soderquist
(74) *Attorney, Agent, or Firm* — Vista IP Law Group LLP

(57) ABSTRACT

A self-shielded, bench-top radiochemistry system, including a radioactive isotope dispensing module configured to draw an isotope out of a vial and dispense one or more metered doses of the isotope to a concentration module that concentrates the metered dose into a droplet amount of isotope and a synthesizer module that delivers the droplet amount of isotope along with one or more reagents to an electrowetting on dielectrics (EWOD) chip to produce a radiolabeled molecule.

19 Claims, 9 Drawing Sheets

(51) Int. Cl.
*A61B 6/00* (2006.01)
*G21H 5/02* (2006.01)
*G21G 1/00* (2006.01)
*G21F 5/015* (2006.01)

(52) U.S. Cl.
CPC ............ *G21G 1/0005* (2013.01); *G21H 5/02* (2013.01); *G21F 5/015* (2013.01)

(58) Field of Classification Search
USPC .......................................................... 436/57
See application file for complete search history.

(56) References Cited

U.S. PATENT DOCUMENTS

| | | | |
|---|---|---|---|
| 6,413,233 B1 | 7/2002 | Sites et al. | |
| 6,565,727 B1 | 5/2003 | Shenderov | |
| 7,452,507 B2 | 11/2008 | Renzi et al. | |
| 7,741,121 B2* | 6/2010 | Elizarov | C07B 59/00 137/625 |
| 7,829,032 B2* | 11/2010 | Van Dam | B01J 19/0093 422/159 |
| 8,071,035 B2* | 12/2011 | Elizarov | B01J 19/0093 422/129 |
| 8,075,851 B2* | 12/2011 | Elizarov | B01F 11/0042 422/502 |
| 8,173,073 B2 | 5/2012 | Elizarov et al. | |
| 8,206,593 B2* | 6/2012 | Lee | B01F 11/0042 210/634 |
| 8,333,952 B2* | 12/2012 | Nutt | A61K 51/0491 422/159 |
| 8,624,039 B2* | 1/2014 | Kim | C07D 207/09 548/567 |
| 8,951,480 B2 | 2/2015 | Satyamurthy | |
| 9,005,544 B2 | 4/2015 | Van Dam et al. | |
| 9,193,640 B2 | 11/2015 | Van Dam et al. | |
| 9,211,520 B2 | 12/2015 | Satyamurthy | |
| 9,421,284 B2* | 8/2016 | Sugita | B01L 3/5027 |
| 9,475,025 B2* | 10/2016 | Samper | B01J 19/0093 |
| 9,481,615 B2 | 11/2016 | Van Dam et al. | |
| 9,481,705 B2 | 11/2016 | Satyamurthy | |
| 9,649,632 B2* | 5/2017 | Van Dam | G01N 35/10 |
| 2003/0057391 A1* | 3/2003 | Krulevitch | F15C 5/00 251/11 |
| 2003/0194039 A1* | 10/2003 | Kiselev | G21G 1/10 376/195 |
| 2003/0211009 A1 | 11/2003 | Buchanan | |
| 2004/0022696 A1 | 2/2004 | Zigler et al. | |
| 2004/0024493 A1 | 2/2004 | Fagrell et al. | |
| 2004/0028573 A1 | 2/2004 | Schmitz et al. | |
| 2004/0258615 A1 | 12/2004 | Buchanan et al. | |
| 2004/0262158 A1* | 12/2004 | Alvord | A61K 51/0402 204/400 |
| 2005/0123420 A1* | 6/2005 | Richter | F04B 43/043 417/413.2 |
| 2005/0147535 A1* | 7/2005 | Shulman | C07B 59/00 422/400 |
| 2005/0226776 A1* | 10/2005 | Brady | B01J 19/0093 422/400 |
| 2005/0232387 A1* | 10/2005 | Padgett | A61K 51/0491 376/194 |
| 2005/0232861 A1 | 10/2005 | Buchanan et al. | |
| 2005/0233078 A1 | 10/2005 | Boyd et al. | |
| 2006/0191926 A1 | 8/2006 | Ray et al. | |
| 2006/0245980 A1 | 11/2006 | Kiselev et al. | |
| 2007/0138076 A1* | 6/2007 | Daridon | G01N 30/6004 210/198.2 |
| 2007/0217963 A1* | 9/2007 | Elizarov | B01F 11/0042 422/130 |
| 2007/0241068 A1 | 10/2007 | Pamula et al. | |
| 2008/0064110 A1* | 3/2008 | Elizarov | C07B 59/00 436/50 |
| 2008/0067413 A1* | 3/2008 | Nutt | G21G 1/0005 250/432 PD |
| 2008/0076914 A1* | 3/2008 | Grigg | A61K 51/0406 536/50 |
| 2008/0131327 A1* | 6/2008 | Van Dam | B01L 3/502715 422/400 |
| 2008/0177126 A1* | 7/2008 | Tate | A61M 5/172 600/5 |
| 2008/0181829 A1* | 7/2008 | Matteo | B01J 19/0093 422/159 |
| 2008/0233018 A1 | 9/2008 | van Dam et al. | |
| 2008/0233653 A1 | 9/2008 | Hess et al. | |
| 2008/0281090 A1* | 11/2008 | Lee | B01F 11/0042 536/122 |
| 2009/0036668 A1 | 2/2009 | Elizarov et al. | |
| 2009/0056861 A1* | 3/2009 | Young | B01F 5/0683 156/221 |
| 2009/0095635 A1* | 4/2009 | Elizarov | C07B 59/00 205/426 |
| 2009/0302228 A1* | 12/2009 | Hadjioannou | B01L 3/502715 250/370.08 |
| 2009/0311157 A1* | 12/2009 | Steel | B01J 19/0093 423/249 |
| 2010/0113762 A1 | 5/2010 | Ball et al. | |
| 2010/0247429 A1* | 9/2010 | Ohsaki | B01D 1/0082 424/1.11 |
| 2011/0008215 A1* | 1/2011 | Elizarov | B01J 19/0093 422/159 |
| 2011/0008223 A1 | 1/2011 | Tsao et al. | |
| 2011/0070158 A1* | 3/2011 | Nutt | A61K 51/0491 424/1.73 |
| 2011/0103176 A1* | 5/2011 | Van Dam | B01F 13/0071 366/154.1 |
| 2011/0129850 A1* | 6/2011 | Tseng | C12M 23/16 435/7.2 |
| 2011/0150714 A1* | 6/2011 | Elizarov | B01J 19/0093 422/159 |
| 2011/0178359 A1* | 7/2011 | Hirschman | G16H 20/17 600/4 |
| 2011/0202177 A1* | 8/2011 | Elizarov | B01J 19/0093 700/268 |
| 2011/0280770 A1* | 11/2011 | Lacy | A61K 51/1282 422/159 |
| 2012/0029209 A1* | 2/2012 | Nakanishi | A61K 51/00 548/542 |
| 2012/0053337 A1* | 3/2012 | Li | C07B 59/005 536/28.54 |
| 2012/0071647 A1* | 3/2012 | Lade | B01F 13/1016 536/122 |
| 2012/0101268 A1 | 4/2012 | Elizarov et al. | |
| 2012/0107175 A1 | 5/2012 | Satyamurthy | |
| 2012/0107185 A1* | 5/2012 | Lebedev | B01J 19/004 422/159 |
| 2012/0108858 A1 | 5/2012 | Kiselev | |
| 2012/0145557 A1* | 6/2012 | Baller | G21G 1/001 205/334 |
| 2012/0178920 A1* | 7/2012 | Kim | C07D 207/09 536/28.8 |
| 2012/0264646 A1 | 10/2012 | Link et al. | |
| 2012/0264932 A1 | 10/2012 | Van Dam et al. | |
| 2012/0305813 A1* | 12/2012 | Knopp | G21F 7/047 250/506.1 |
| 2013/0020727 A1 | 1/2013 | Klausing et al. | |
| 2013/0023657 A1* | 1/2013 | Klausing | G01N 30/88 536/28.2 |
| 2013/0053994 A1* | 2/2013 | Rensch | G16H 40/63 700/95 |
| 2013/0102772 A1* | 4/2013 | Eshima | G21G 1/10 536/28.2 |
| 2013/0108513 A1* | 5/2013 | Samper | B01J 19/0093 422/129 |
| 2013/0130309 A1* | 5/2013 | Nutt | G01N 30/74 435/35 |
| 2013/0170931 A1 | 7/2013 | Samper et al. | |
| 2013/0240449 A1* | 9/2013 | Collier | G01N 30/20 210/656 |
| 2013/0334443 A1 | 12/2013 | Steel et al. | |

(56) References Cited

U.S. PATENT DOCUMENTS

| | | | | |
|---|---|---|---|---|
| 2013/0337493 | A1* | 12/2013 | Hansteen | G01N 21/31 435/34 |
| 2014/0120010 | A1* | 5/2014 | Rensch | B01L 3/502707 422/503 |
| 2014/0170758 | A1* | 6/2014 | Baller | B01J 19/004 436/58 |
| 2014/0208832 | A1* | 7/2014 | Hansen | G01N 13/00 73/53.01 |
| 2015/0004060 | A1* | 1/2015 | Langstrom | G21F 7/015 422/111 |
| 2015/0064071 | A1* | 3/2015 | Lambert | B01J 19/0093 422/159 |
| 2015/0086476 | A1* | 3/2015 | Eriksson | C07B 59/00 424/1.11 |
| 2015/0148549 | A1 | 5/2015 | Van Dam et al. | |
| 2015/0152206 | A1* | 6/2015 | Keng | B01J 20/3204 522/185 |
| 2015/0157743 | A1* | 6/2015 | McFarland | A61K 51/025 424/1.89 |
| 2015/0182963 | A1* | 7/2015 | Samper | B01J 19/0093 422/502 |
| 2015/0182964 | A1* | 7/2015 | Samper | B01L 3/502746 137/1 |
| 2015/0203416 | A1 | 7/2015 | Van Dam et al. | |
| 2015/0301204 | A1* | 10/2015 | Srivastava | G01T 1/10 422/119 |
| 2015/0329583 | A1 | 11/2015 | Satyamurthy | |
| 2016/0003791 | A1* | 1/2016 | Lebedev | G01N 33/15 422/82.05 |
| 2016/0107951 | A1 | 4/2016 | Van Dam et al. | |
| 2016/0130295 | A1 | 5/2016 | Satyamurthy | |
| 2016/0280734 | A1 | 9/2016 | Moore et al. | |

FOREIGN PATENT DOCUMENTS

| | | |
|---|---|---|
| JP | 01139591 | 6/1989 |
| JP | 03-11617 | 1/1991 |
| JP | 2009-047454 A | 3/2009 |
| JP | 2010-260799 | * 11/2010 |
| JP | 2012-229968 | * 11/2012 |
| JP | 2013-508129 A | 3/2013 |
| KR | 10-2013-002795 A | 3/2013 |
| WO | WO03/078358 | 9/2003 |
| WO | WO 2004/030820 | 4/2004 |
| WO | WO2004/062779 | 7/2004 |
| WO | WO 2006/018088 | 2/2006 |
| WO | WO 2006/071470 | 7/2006 |
| WO | WO 2006/124458 | 11/2006 |
| WO | WO2006/134035 | 12/2006 |
| WO | WO 2007/120241 | 10/2007 |
| WO | WO 2008/091694 A2 | 7/2008 |
| WO | WO 2011/046615 A2 | 4/2011 |

OTHER PUBLICATIONS

Wang, M.-W. et al, Molecular Imaging 2010, 9, 175-191.*
Kealey, S. et al, Organic & Biomolecular Chemistry 2011, 9, 3313-3319.*
Keng, P. Y. et al, Proceedings of the National Academy of Sciences 2012, 109, 690-695.*
Ding, H. et al, Lab on a Chip 2012, 12, 3331-3340.*
Chen, S. et al, "Synthesis of diverse tracers on EWOD microdevice for positron emission tomography (PET)" Solid-State Sensors, Actuators and Microsystems Workshop, Hilton Head Island, SC, Jun. 3-7, 2012, 189-192.*
Lebedev, A. et al, Lab on a Chip 2013, 13, 136-145.*
Jebrail, M. J. et al, Analytical Chemistry 2014, 86, 3856-3862.*
Javed, M. R. et al, Journal of Nuclear Medicine 2014, 55, 321-328.*
Herman, H. et al, Applied Radiation and Isotopes 2013, 78, 113-124.*
Shah, G. J. et al, Lab on a Chip 2013, 13, 2785-2795.*
Lazari, M. et al, EJNMMI Research 2013, 3, paper 52, 13 pages.*
Yi, Ui-Chong et al., Soft Printing of Droplets Pre-Metered by Electrowetting, Sensors and Actuators A, 2004, 114 (2-3), 347-354.
Colon, Luis et al., Very high pressure HPLC with 1 mm id columns, Analyst, 2004, 129, pp. 503-504.
Reichmuth, David S. et al., Microchip HPLC of Peptides and Proteins, Anal. Chem. 2005, 77, 2997-3000.
Shih, Steve C.C. et al., Dried Blood Spot Analysis by Digital Microfluidics Coupled to Nanoelectrospray Ionization Mass Spectrometry, Anal. Chem. 2012, 84, 3731-3738.
Shah, G. J. et al., Integrated digital microchemistry platform: Automation of multi-reagent loading, on-chip high-temperature reactions, and product extraction, Intl. Symposium on Microchemistry and Microsystems, Zhubei, Taiwan, Jun. 2012, abstract, 2 pages.
Elizarov, Arkadij et al., Design and Optimization of Coin-Shaped Microreator Chips for PET Radiopharmaceutical Synthesis, J. Nucl Med 51(2): 282 (2010).
PCT International Search Report for PCT/US2013/045030, Applicant: The Regents of the University of California, Form PCT/ISA/210 and 220, dated Sep. 11, 2013 (6 pages).
PCT Written Opinion of the International Search Authority for PCT/US2013/045030, Applicant: The Regents of the University of California,, Form PCT/ISA/237, dated Sep. 11, 2013 (5 pages).
Zhao et al., Digital Microfluidic Chips for Automated Hydrogen Deuterium Exchange (HDX) MS Analysis, 15th Int'l Conference on Miniaturized Systems for Chemistry and Life Sciences, Oct. 2-6, 2011, Seattle, WA, USA, pp. 1287-1289.
PCT International Preliminary Report on Patentability (Chapter I of the Patent Cooperation Treaty) for PCT/US2013/045030, Applicant: The Regents of the University of California, Form PCT/IB/326 and 373, dated Dec. 18, 2014 (7pages).
Shah, G.J. et al., Milliliter-to-Microliter Platform for On-Demand Loading of Aqueous and Non-Aqueous Droplets to Digital Microfluidics, Transducers' 11, Beijing, China, Jun. 5-9, 2011, 1260-1263.
PCT International Preliminary Report on Patentability (Chapter I of the Patent Cooperation Treaty) for PCT/US2015/034583, Applicant: The Regents of the University of California, Form PCT/IB/326 and 373, dated Dec. 15, 2016 (6pages).
The extended European search report dated Jan. 23, 2018 in European Patent Application No. 15803109.6, Applicant: The Regents of the University of California, (6pages).
Elizarov, Arkadij, Microreactors for Radiopharmaceutical Synthesis, Lab Chip, 2009, 9, 1326-1333.
Fan, Shih-Kang et al., EWOD Driving of Droplet on NxM Grid Using Single-Layer Electrode Patterns, Solid-State Sensor, Actuator and Microsystems Workshop, Hilton Head Island, South Carolina, Jun. 2-6, 2002.
Audrain, Helene, Positron Emission Tomography (PET) and Microfluidic Devices: A Breakthrough on the Microscale?, Angew. Chem. Int. Ed. 2007, 46, 1772-1775.
Lee, Chung-Chen et al., Multistep Synthesis of a Radiolabeled Imaging Probe Using Integrated Microfluidics, Science, vol. 310, Dec. 16, 2005, 1793-1796.
Written Opinion and Search Report of International Application No. PCT/US2009/004745 dated Jan. 19, 2010.
Lindsey, J.S., A Retrospective on the Automation of Laboratory Synthetic Chemistry, Laboratory Automation & Information Management, Elsevier Science Publ. BV., Amsterdam, NL, vol. 17, No. 1, Oct. 1, 1992, pp. 15-45.
Mangner, Thomas J. et al., Synthesis of 2'-deoxy-2'-[18F]fluoro-B-D-arabinofuranosyl nucleosides, [18F]FAU, [18F]FMAU, [18F]FBAU and [18F]FIAU, as potential PET agents for imaging cellular proliferation, Nuc.Med. Bio., 30, pp. 215-224 (2003).
Pankiewicz, Krzysztof W. et al., A Synthesis of 9-(2-Deoxy-2-fluoro-B-D-arabinofuranosyl)adenine and Hypoxanthine. An Effect of C3'-Endo to C2'-Endo Conformational Shift on the Reaction Course of 2'-Hydroxyl Group with DAST1, J. Org. Chem. 57, 553-559 (1992).
Tann, Chou H. et al., Fluorocarbohydrates in Synthesis. An Efficient Synthesis of 1-(2-Deoxy-2-fluoro-B-D-arabino-furanosyl)-5-iodouracil (B-FIAU) and 1-(2-Deoxy-2-fluoro-B-D-arabinofuranosyl)thymine (B-FMAU), J. Org. Chem. 50, 3644-3647 (1985).

(56) References Cited

OTHER PUBLICATIONS

Alauddin, Mian M. et al., Synthesis of [18F]-labeled adenosine analogues as potential PET imaging agents, J Label Compd Radiopharm 2003; 46: 805-814.
Alauddin, Mian M. et al., Synthesis of [18F]-labeled 2'-deoxy-2'-fluoro-5-methyl-1-B-D-arabinofuranosyluracil([18F]-FMAU), J Label Compd Radiopharm 2002; 45: 583-590.
Anderson, Harry et al., Improved synthesis of 2'-deoxy-2'-[18F]-fluoro-1-B-D-arabinofuranosyl-5-iodouraci ([18F]-FIAU), Nuclear Medicine and Biology 37 (2010) 439-442.
Cai, Hangcheng et al., The improved synthesis of 5-substituted 2'-[18F]fluoro-2'-deoxy-arabinofuranosyluracil derivatives ([18F]FEAU, [18F]FFAU, [18F]FCAU, [18F]FBAU and [18F]FIAU) using a multistep one-pot strategy, Nuclear Medicine and Biology 38 (2011) 659-666.
Chin, Frederick T. et al., Semiautomated Radiosynthesis and Biological Evaluation of [18F]FEAU: A Novel PET Imaging Agent for HSV1-tk/sr39tk Reported Gene Expression, Mol Imaging Biol (2008) 10:82-91.
Coenen, H.H. et al., Fluorine-18 radiopharmaceuticals beyong [18F]FDG for use in oncology and neurosciences, Nuclear Medicine and Biology 37 (2010) 727-740.
Herman, Henry et al., Multi-pot radiosynthesizer capable of high-pressure reactions for production of [18F]FAC and analogs, J. Nucl Med. 2011; 52 (Supplement 1):1440.
Herman, Henry et al., Flexible radiosynthesizer capable of multi-pot high temperature and pressure reactions, Crump Institute Molecular Imaging, UCLA, Department of Molecular & Medical Pharmacology, UCLA, Sofie Biosciences, Inc. (PPT) (2011) (24pages).
Herman, Henry et al., Flexible radiosynthesizer capable of multi-pot high temperature and pressure reactions, Crump Institute Molecular Imaging, UCLA, Department of Molecular & Medical Pharmacology, UCLA, Sofie Biosciences, Inc. (Abstract) (2011) (1page).
Keng, Pei Yuin et al., Emerging Technologies for Decentralized Production of PET Tracers, Positron Emission Tomography—Current Clinical and Research Aspects, www.intechopen.com, InTech; 2012; 153-182.
Li, Zibo et al., Automated synthesis of 2'-deoxy-2'-[18F]fluoro-5-methyl-1-B-D-arabinofuranosyluracil ([18F]-FMAU) using a one reactor radiosynthesis module, Nuclear Medicine and Biology 38 (2011) 201-206.

Moore, Melissa D. et al., ARC-P HS+: A versatile radiosynthesizer for the production of PET tracers, AACR Annual Meeting, Mar. 31-Apr. 4, 2012, Chicago, IL (1page).
Paolillo, Vincenzo et al., A fully automated synthesis of [18F]-FEAU and [18F]-FMAU using a novel dual reactor radiosynthesis module, J. Label Compd. Radiopharm 2009, 52, 553-558.
Sachinidis, John I et al., Automation for Optimised Production of Fluorine-18-Labelled Radiopharmaceuticals, Current Radiopharmaceuticals, 2010, 3, 248-253.
PCT International Search Report for PCT/US2014/031905, Applicant: The Regents of the University of California, Form PCT/ISA/210 and 220, dated Jul. 25, 2014 (5pages).
PCT Written Opinion of the International Search Authority for PCT/US2014/031905, Applicant: The Regents of the University of California Form PCT/ISA/237, dated Jul. 25, 2014 (5pages).
PCT International Preliminary Report on Patentability (Chapter I of the Patent Cooperation Treaty) for PCT/US2014/031905, Applicant: The Regents of the University of California, Form PCT/IB/326 and 373, dated Oct. 8, 2015 (7pages).
PCT International Search Report for PCT/US2015/034583, Applicant: The Regents of the University of California et al., Form PCT/ISA/210 and 220, dated Sep. 24, 2015 (5pages).
PCT Written Opinion of the International Search Authority for PCT/US2015/034583, Applicant: The Regents of the University of California et al., Form PCT/ISA/237, dated Sep. 24, 2015 (4pages).
Communication pursuant to Rules 70(2) and 70(a) EPC in European Patent Application No. 15803109.6-1109, dated Feb. 9, 2018, (1page).
van Dam, R. Michael et al., Automated Microfluidic-Chip-Based Stand-Alone Instrument for the Synthesis of Radiopharmaceuticals on Human-Dose Scales, NSTI-Nanotech 2007, www.nsti.org, ISBN 1420061844, vol. 3, 2007.
Wang, Ming-Wei et al., Microfluidics for Positron Emission Tomography (PET) Imaging Probe Development, Mol Imaging. Aug. 2010; 9(4): 175-191.
Communication pursuant to Article 94(3) EPC dated Dec. 3, 2017 in European Patent Application No. 15803109.6, (3pages).
Communication pursuant to Article 94(3) EPC dated Dec. 3, 2018 in European Patent Application No. 15803109.6-1109, Applicant: The Regents of the University of California, (3pages).
Notice of Rejection dated Apr. 2, 2019 in Japanese Patent Application No. 2017-516644, Applicant: The Regents of the University of California, (8pages).

* cited by examiner

SELF-SHIELDED, BENCHTOP RADIO CHEMISTRY SYSTEM WITH A PLURALITY SHIELDED CARRIERS CONTAINING A DISPOSABLE CHIP CASSETTE

CROSS-REFERENCE TO RELATED APPLICATIONS

This application is a U.S. National Stage filing under 35 U.S.C. § 371 of International Application No. PCT/US2015/034583, filed Jun. 5, 2015, which claims priority to, and the benefit of, U.S. provisional patent application Ser. No. 62/008,997 filed on Jun. 6, 2014, incorporated herein by reference in its entirety. Priority is claimed pursuant to 35 U.S.C. § 119 and any other applicable statute.

STATEMENT REGARDING FEDERALLY SPONSORED RESEARCH OR DEVELOPMENT

This invention was made with government support under Grant Number DE-SC0006238, awarded by the U.S. Department of Energy and Grant Number MH097271, awarded by the National Institutes of Health. The government has certain rights in the invention.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to a chemistry system for three-dimensional (3D) imaging, and more particularly to a bench-top radiochemistry system for 3D imaging.

2. Background Discussion

Positron Emission Tomography (PET) is a dynamic 3D imaging modality that can be used for microorganisms, cells, animals, plants, and humans to quantitatively measure biochemical processes in vivo. It uses "probes" (e.g. small molecules, peptides, proteins, nanoparticles, etc.) that are labeled with positron-emitting radioisotopes such as fluorine-18, carbon-11, nitrogen-13, oxygen-15, iodine-124, and copper-64, which interact on a molecular level with the biological system under study. Thus, PET can provide insight into various functional questions about biology, such as the distribution of metabolic activity (rate) in an organism, the spatial distribution of a target (e.g. cell surface marker or receptor); the movement of cells or microorganisms, the quantification of gene expression levels, the pharmacodynamics and pharmacokinetics of drug perturbation, and many other processes. Due to the high sensitivity of radiation detectors, PET is extremely sensitive compared to other imaging modalities, and can be accomplished with trace amounts of the probe, thereby not further perturbing the biological system under study. Additionally, due to the ability of energetic gamma rays (emitted after annihilation of positrons) to penetrate thick objects, PET can quantitatively image deep inside animal and plant tissues, enabling visualization of processes that cannot be easily seen with optical methods involving fluorescence or bioluminescence. Thus, PET provides a powerful way to safely study biology that can be translated across cells, plants, animals, and humans.

While PET would offer many advantages to the research community if a diversity of probes were routinely available, accessibility to the ~3,000 known probes is very limited. In fact, the majority of PET studies (~90%) employ only one probe, the glucose analog, 2-fluoro-2-deoxy-D-glucose (FDG). Due to their short half-life, as determined by the radioactive isotope they are tagged with (i.e. fluorine-18, ~110 min), probes must be chemically synthesized immediately before use in a manner that provides safety and reliability to the user. Currently, PET probe production is expensive and requires a large capital investment in infrastructure (e.g. cyclotrons, cumbersome lead-shielded chemistry "hot cells", purification systems, etc.) and specially trained personnel (for radiochemistry and cyclotron operation). Thus, the bulk of PET probes are produced in a centralized manner by commercial PET radiopharmacies established for clinical use of PET, with limited capacity and expertise, and high operating costs that restrict them from including production of new imaging probes. A number of universities have the same infrastructures as the commercial radiopharmacies. In these academic programs, production of probes is also complex, costly, and maintains a limited capacity to provide the diversity in molecular probes that matches the diversity of disciplines and biological problems to be studied.

BRIEF SUMMARY

The present description details a new hybrid approach in contrast to the established, centralized approach, by providing both the traditional radiopharmacies and researchers/clinicians (decentralized model) with the technology to produce on-demand batches of their PET probe of interest in an automated, user-friendly, device with low overall cost.

The systems and methods of the present disclosure use microfluidics for the integration of unit operations of chemical synthesis, purification, and quality control (QC) into a compact, inexpensive, self-shielded device. With the technology of the present disclosure, one would simply need a supply of the radioisotope from commercial radiopharmacies and a kit comprising one-use reagents and a chip. Such systems provide vast improvements to the research and clinical production field by providing the freedom for scientists in diverse disciplines to use molecular imaging probes of their choice without the normal infrastructure, expense, and complexity that is normally associated in existing systems.

In a preferred embodiment of the present disclosure, the system is configured to be operated without a hot cell, allows multiple radiosynthesis runs from a single batch of radioisotope, and ensures that the user is not exposed to radiation when changing a disposable cassette between one radiosynthesis and the next. In another embodiment, the batch of radioisotope can be safely changed without waiting for radioactive decay.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
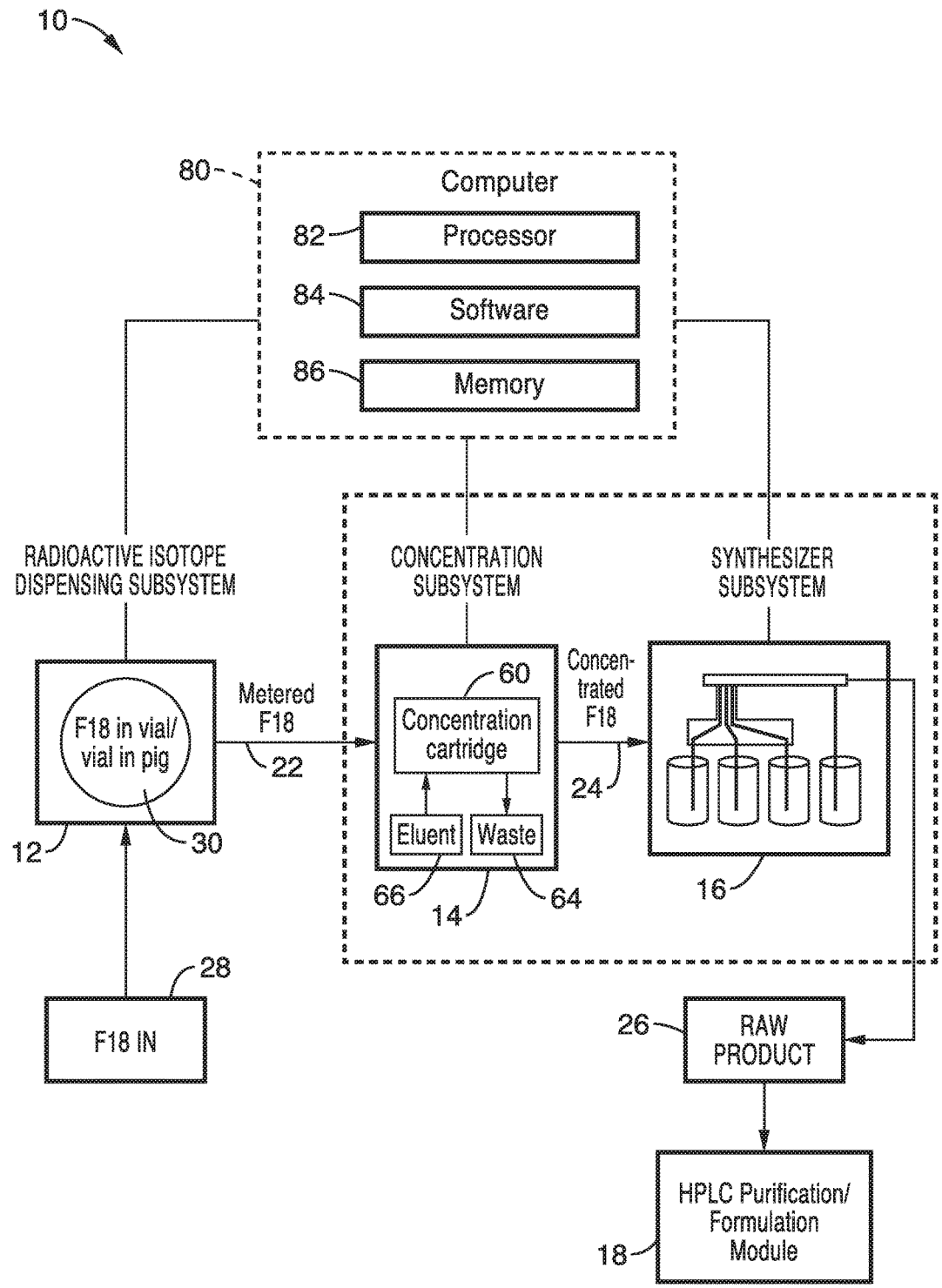
FIG. 1 shows a high-level schematic diagram of a self-shielded, bench-top radiochemistry system in accordance with the present description.

For purposes of the following description, the following terms are defined as follows:

A "radiopharmaceutical" (e.g. "PET probe", "PET tracer") is a radioactive pharmaceutical. Radiopharmaceuticals are used in the field of nuclear medicine as tracers in the diagnosis and treatment of many diseases. Radiopharmaceuticals are more commonly known and detailed in the context of this disclosure as a "PET probe" or "PET tracer."

"Positron Emission Tomography (PET) Imaging" is a nuclear medical imaging technique that produces a three-dimensional image or picture of functional processes in the body. A radioactive PET probe is injected into the patient before they are placed into the PET scanner; the PET scanner is a camera that detects the location of the PET probe in the patient's body.

As the radioactive isotope on the PET probe undergoes positron emission decay (also known as positive beta decay), it emits a positron, an antiparticle of the electron with opposite charge. The emitted positron travels in tissue for a short distance (typically less than 1 mm, but this depends on the isotope), during which time it loses kinetic energy, until it decelerates to a point where it can interact with an electron. The encounter annihilates both electron and positron, producing a pair of annihilation (gamma) photons moving in approximately opposite directions (two 511 keV gamma photons being emitted at almost 180 degrees to each other). These are detected when they reach a scintillator in the scanning device, creating a burst of light, which is detected by photomultiplier tubes or silicon avalanche photodiodes (Si APD). The technique depends on simultaneous or coincident detection of the pair of photons moving in approximately opposite direction (it would be exactly opposite in their center of mass frame, but the scanner has no way to know this, and so has a built-in slight direction-error tolerance). Photons that do not arrive in temporal "pairs" (i.e. within a timing-window of a few nanoseconds) are ignored.

"Reagents" are any biological or chemical entity that participates in synthesis.

"Synthesis" is the action of chemically adding the radioactive isotope to another entity, e.g. a small molecule, a protein, a peptide, an antibody, etc.

"Positron emitters" are any radioactive isotope that can be used in PET imaging (e.g. C11, F18, O16, Ga68, etc.).

A "radiosynthesizer" is a radiochemistry synthesizer, e.g. device used in the synthesis of PET probes. F-18 is a fluorine radioisotope, which is an important source of positrons. It has a half-life of 109.771 minutes. It decays by positron emission 97% of the time and electron capture 3% of the time. Both modes of decay yield stable oxygen-18 (see O-18).

"O-18", or "Oxygen-18," is a natural, stable isotope of oxygen. Enriched water (H2O^18) is bombarded with hydrogen ions in either a cyclotron or linear accelerator creating fluorine-18 (see F-18).

"Specific activity" is generally defined as the amount of radioactivity per unit mass of the labeled compound. The mass of the labeled compound includes the mass of the radioactive product as well as the mass of the nonradioactive counterpart. Generally given in Ci/mmol. When dealing with the production of PET probes, it's important to minimize the isotopic dilution (contamination from stable isotopes of the same element). For example, in the production of F18, it is desirable to minimize the amount of F19 in the sample). The extent of isotopic dilution is determined by the measurement of the specific activity of the probe.

A "cyclotron" is a type of particle accelerator in which charged particles accelerate outwards from the center along a spiral path, and is typically used in the production of PET isotopes, specifically F-18.

"Pig" refers to the lead or tungsten holder that allows safe and shielded transport of radioactive compounds.

A "cartridge" is a container that holds a filter, absorbent material, chemical substance, or combination of these items that alternately binds and releases substances passing through it. Depending on what it is packed with, a cartridge may also be referred to as "QMA" or "SPE."

"Eluent" is a liquid used to remove substances trapped on a cartridge

"Shine" is direct radiation emitted from the radioactive source.

"Radioactivity" is referred to as the emission of ionizing radiation or particles caused by the spontaneous disintegration of atomic nuclei.

"Hot" refers to parts of the system that are radioactive and must be shielded. "Cold" refers to nonradioactive, non-shielded areas.

"Half-life" refers to the amount of time required for a quantity to fall to half its value as measured at the beginning of the time period. While the term "half-life" can be used to describe any quantity which follows an exponential decay, for purposes of the present disclosure the term "half-life" is used to define the time required, probabilistically, for half of the unstable, radioactive atoms in a sample to undergo radioactive decay.

"Radiopharmacy"/"Radiochemistry core" refers to any facility that has a cyclotron and produces radioactive isotopes for PET probe synthesis on demand. This can be both commercial (e.g. PETNET, Cardinal Health, etc.) or academic (e.g. UCLA's Crump Center, UCLA's Ahamanson center).

"Preclinical" refers to experiments conducted on any system (cells, animals), not including humans. "Clinical" refers to studies conducted on humans.

"Customer" refers to people/entities generally falling into 3 main categories: 1) preclinical researchers who want to introduce (and control) PET imaging in their own lab, 2) radiopharmacies/radiochemistry cores that have a dedicated infrastructure to supply PET probes, but are looking to branch out in the menu of probes that they supply to customers, and 3) clinicians who have PET scanners in their facility and want a diversity of FDA-approved or clinical research probes (probes in clinical trials) to give to their patients/study subjects.

FIG. 1 shows a high-level schematic diagram of a self-shielded, bench-top radiochemistry system 10 in accordance with the present description. Radiochemistry system 10 comprises four primary integrated subsystems: a radioactive isotope dispensing module or subsystem 12; a concentration module or subsystem 14; a synthesizer module or subsystem 16; and an HPLC and Cartridge based Purification/Formulation module or subsystem 18.

The radioactive isotope dispensing subsystem 12 draws isotope (e.g. F18) out of shipping vial or vial in pig 28, quantifies radioactivity, and dispenses user-defined aliquots (metered F18 fluid plug 22) to the concentration subsystem 14. In a preferred embodiment, the radioactive isotope (1-30 mL of liquid form) comes in a 30 mL sealed glass vial 28 (13 mm septum topped and crimp capped) held in a tungsten or lead pig 30. Alternatively, the radioactive isotope could come in a different type of vial (5 mL v-vial), Eppendorf tube, syringe, or direct line from a generator or cyclotron (not shown).

In the concentration subsystem 14, the aliquot of isotope is pushed through a concentrator cartridge 60 (see FIG. 6) and waste 66 is recovered; eluent 64 is pushed through the concentrator 60 to bring droplet amount of isotope to chip.

The synthesizer subsystem 16 brings reagents (including concentrated radioactive isotope 24 from concentration subsystem 14) to the chip, and includes a disposable cassette 80 for all wetted paths and shielding for waste management, and performs synthesis of crude (unpurified) PET probe. It is noted that the concentration subsystem 14 and synthesizer subsystem 16 may occupy the same space, and/or use the same elements, as their consumables are changed at the same frequency.

Purification/Formulation module 18 removes crude (unpurified) PET probe 26 from the chip, passes it through a cartridge or HPLC column (both accounted for in system), collects purified product into a shielded container, and puts the purified product into proper volume and solution. For the purpose of the present description, cartridge purification (for FDG) is considered.

Computer 80 may also be coupled to each of the subsystems to control calibration and operation of various processes via software 84 stored in memory 86 and executable on processor 82.

Figure 2:
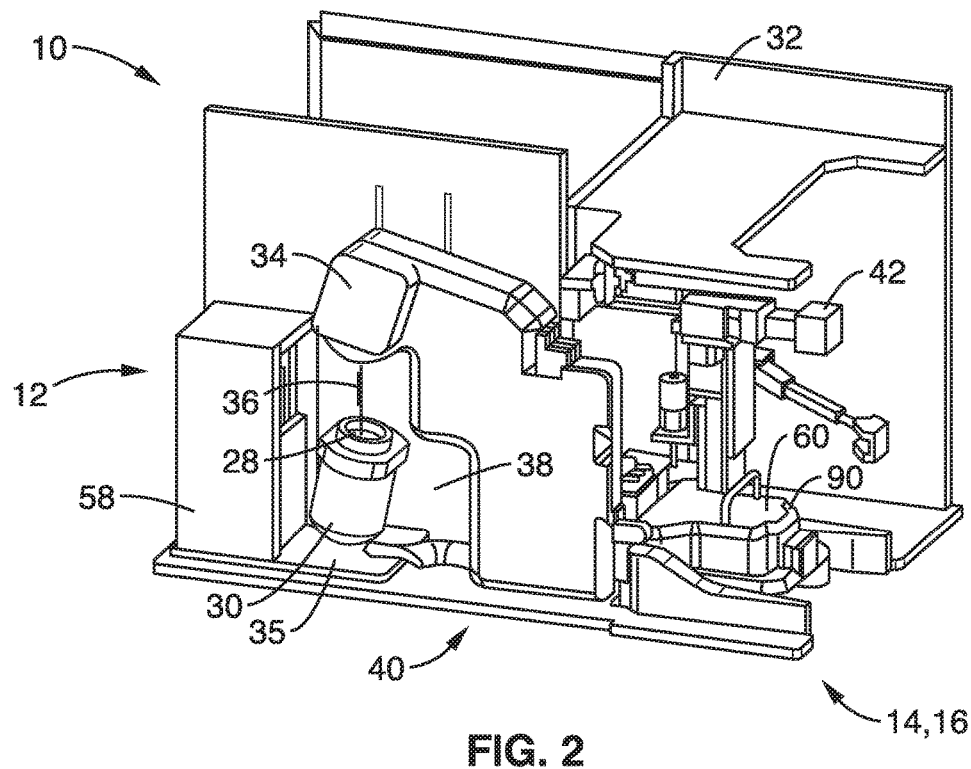
FIG. 2 shows a perspective view of a fully-integrated chip-based chemical synthesizer in accordance with the system of FIG. 1.

FIG. 2 shows a perspective view of a fully-integrated chip-based chemical synthesizer 10 so that fluidic, electrical, and mechanical connections run from each subsystem to the next, without loss of fluid or radioactivity.

In a preferred embodiment, the workflow is as follows. First, a user places pig 30 with radioactive isotope vial 28 in synthesizer 12. A drawer (not shown) may be available on the front of the device housing 32 to allow the user to place the pig 30 into a cavity 38 of housing. The user assembles other subsystem cassettes (e.g. cassette 80 (FIG. 1)) into the synthesizer 10 or removable shielded holder 34.

If it is the first run of the day, the user interacts with the provided software 84 by first inputting some information about the radioactive isotope 28 (e.g. which isotope, amount of radioactivity, time, etc.). This information may be available from a label on the tungsten pig 30.

The user chooses from list of PET probes and indicates how much activity should be delivered to the synthesis subsystem, and the amount of radioactivity to start the synthesis with (or the user may select the final amount of synthesizer/purified/formulated probe desired, and the system calculates the corresponding starting activity based on the synthesis time and expected yield. The system 10 self-calibrates the radioactivity concentration, and then makes calculations to determine the proper volume to be dispensed.

The synthesizer 10 runs through all subsystems without user intervention. The system 10 (e.g. via software) alerts the user that the run is complete and the user removes the shielded pig 30 with the purified and formulated product in the vial for use in PET imaging. The user removes the used and radioactive reagent-chip-concentrator cassette 90 in a removable shielded holder (if HPLC is used, the system cleans the purification system). If the next user needs a different radioactive isotope (e.g. F-18 vs. Ga-68) or different isotopes are used on the same day (i.e. before the radioactivity has decayed to background levels), the radioactive isotope-dispensing cassette 40 is removed. This could be accomplished either by replacing the whole shielded cassette with a new shielded cassette, or by opening the dose dispensing cassette shielding and replacing just the cassette. In a preferred embodiment, all wetted components of the dose dispensing cassette 40 are disposable, and all paths that contain radioactivity are shielded by material capable of attenuating beta and gamma rays. In a preferred embodiment, all materials are solvent-resistant.

Figure 3:
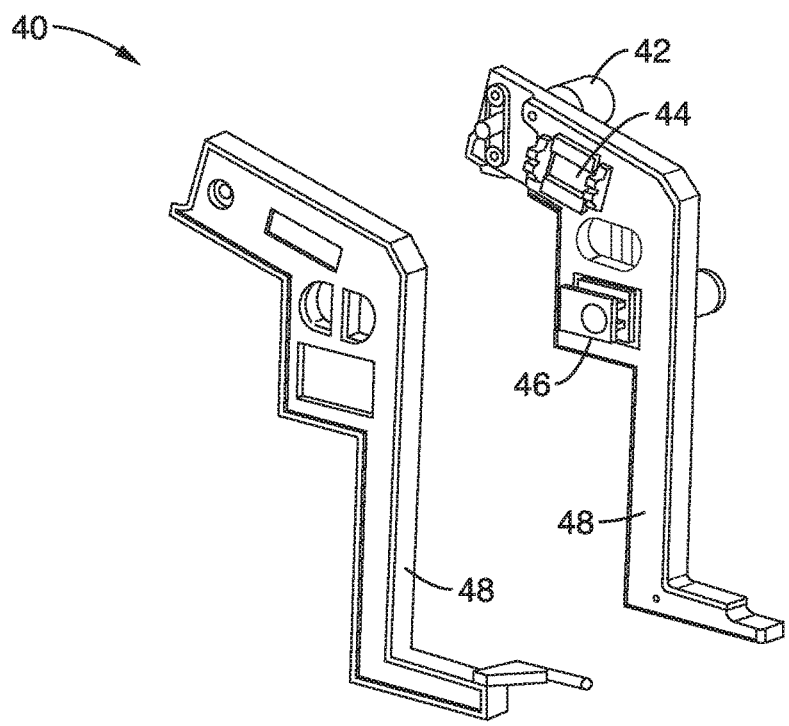
FIG. 3 shows a perspective view of a dose dispensing cassette that may be used in the dispensing subsystem of FIG. 1 and FIG. 2.
Figure 4:
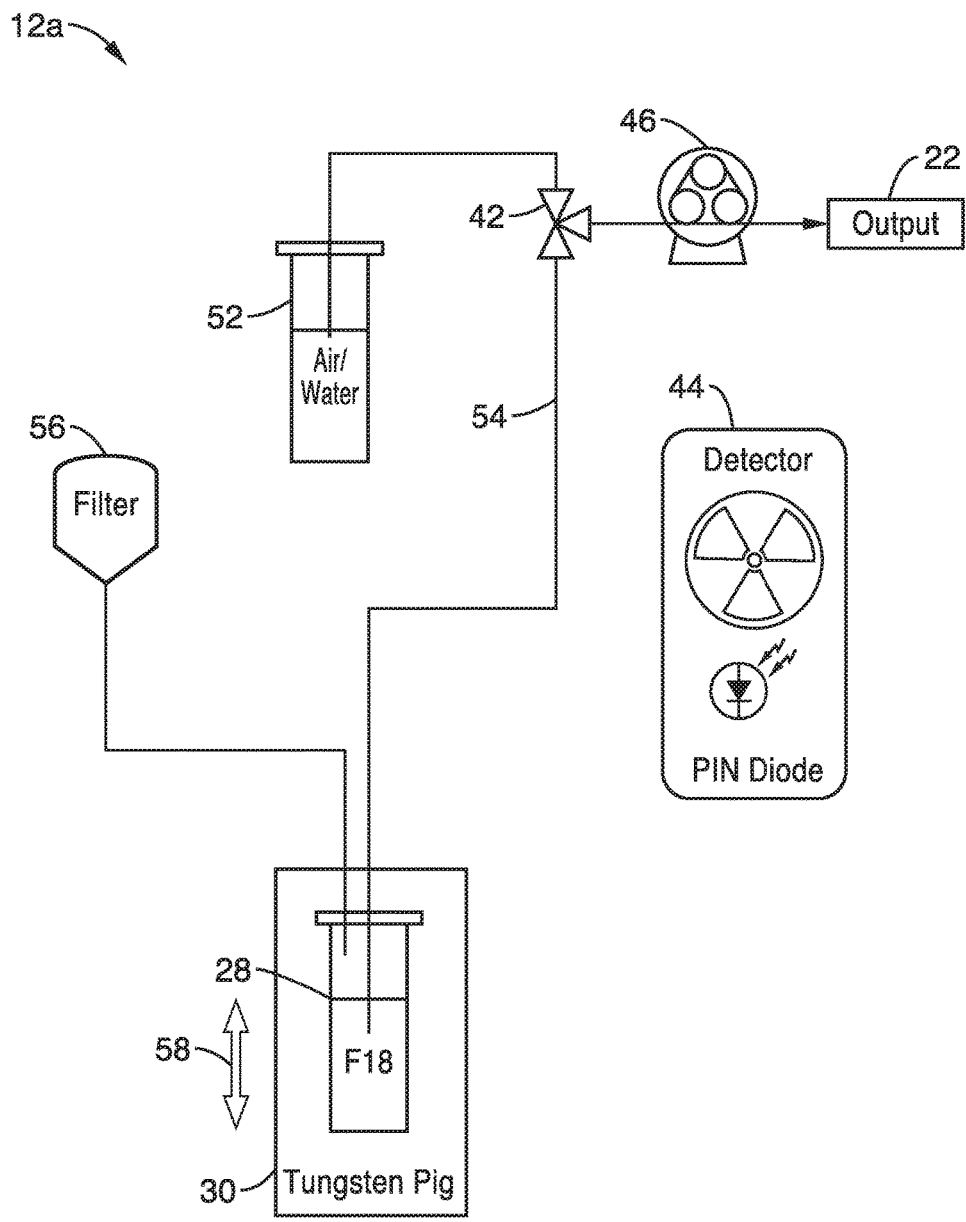
FIG. 4 shows a schematic diagram of an embodiment dispensing subsystem.
Figure 5:
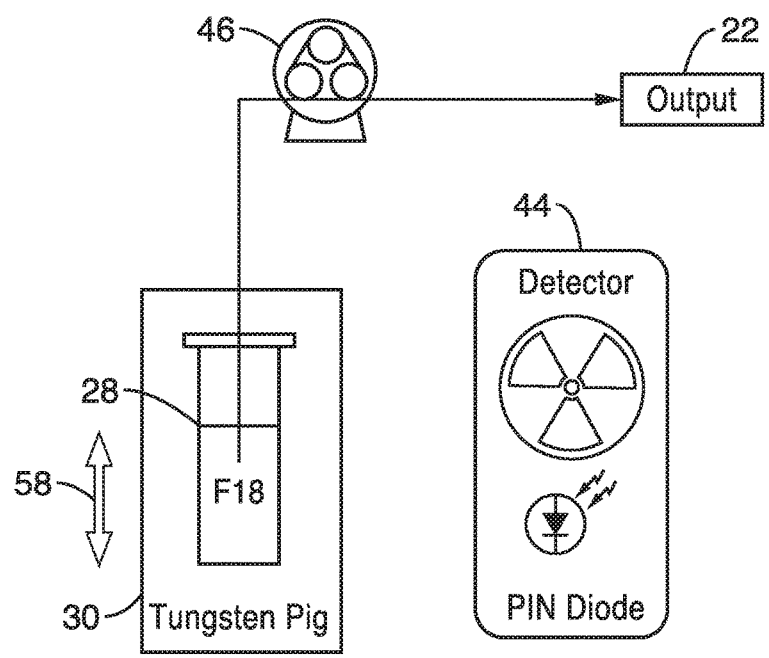
FIG. 5 shows a schematic diagram of an alternative embodiment dispensing subsystem without valves.

FIG. 3 shows a perspective view of the dose dispensing cassette 40 which may be used in the dispensing subsystem 12 of FIG. 1 and FIG. 2, and dispensing subsystem variations 12a and 12b shown schematically in FIG. 4 and FIG. 5, respectively. The dose dispensing subsystem 12 has several purposes: a) determine the radioactivity concentration of the liquid in the vial 28 via a radiation detector 44, b) calculate the volume of fluid that contains a desired amount of activity based on radioactivity decay since the calibration measurement, c) dispense that amount of activity from the source and meter it to downstream subsystems, d) provide shielding to reduce/remove radiation exposure to the operator.

First, the dispensing system 12 lifts the ~10 lb pig 30 up (e.g. via linear actuator 58 and elevator platform 35 shown in FIG. 2) so a disposable needle 36 (held fixed) pierces the septum and reaches the bottom of the vial 28. Because the vial 28 comprises a flat-bottom, the dose dispenser housing 34 holds the pig 30 at an angle to recover as much of the radioactive isotope as possible.

A pliable tube (not shown) made from a silicone material is connected to the needle 36 and runs through a pump 46, which is fixed to housing 48 of dispensing cassette 40 (see FIG. 3). In one embodiment, the pump 46 comprises a peristaltic pump that provides the necessary negative pressure to draw the radioactive isotope solution out of the vial 28. Other types of pumps known in the art are also contemplated, e.g. the pump 46 may also comprise a membrane type of pump (comprising a deformable membrane between two valves (not shown)) It should be noted that the tubing and needle may become part of the easily inserted and removed disposable cassette 40 of FIG. 3.

The first time the fluid path is filled, the fluid is stopped and a radiation sensor 44 measures the amount of radioactivity in the tubing. In a preferred embodiment, the sensor 44 comprises a dual pin diode detector for sensing a gamma photon signal that can be used to obtain dose information. Because the geometry of the tubing and sensor are precisely fixed (and consistent from cassette to cassette), the sensor reading provides a measure of the activity concentration of the isotope. Calibration may be performed at the time a dose is requested, though it may be preferable to perform the calibration as soon as the pig is installed (see above). Calibration is only performed once for each batch of radioisotope (thus, for this generation of the system, once per day).

The dispensing subsystem 12a dispenses fluid until the requested volume (computed from the requested activity) is in the fluid line. Then the valve 42 on the output changes state. This allows the output metered volume fluid plug 22 to be driven by gas pressure to the concentration subsystem. The dispensing subsystem 12a then may retract the remaining fluid in the lines back into the radioactive isotope source vial 28, minimizing the activity outside of the pig 30. This reduces the radiation exposure to users from activity that remains in the tubing when this subsystem is not being utilized. During the retraction phase a valve (or alternate mechanism) may be used to disconnect this subsystem from the next subsystem and the peristaltic pump 46 may run in reverse. This is because the next two subsystems 14 and 16 have disposable components that are ideally replaced after every synthesis, while the isotope dispensing subsystem's disposable parts only need to be replaced once per day.

However, it is also appreciated that an alternative embodiment may have the needle and dispensing fluid path may be integrated into a disposable cassette that also houses the concentrator module 14 and the synthesis module 16, if so desired. This configuration would still interface with the shielded vial 30, elevator 35, and radiation sensor 44 as provided in FIG. 3. The needle 36 may also be configured to use a 'swing-down' mechanism (not shown) so that the user is protected during handling and the system swings down the needle when installed (and returns it to protected position prior to the user removing this cassette).

The radioactive isotope dispensing subsystem 10 outputs metered "activity" fluid plugs 22 to the concentration subsystem 14. The activity is defined by the user and may be requested via a USB or Ethernet connection (not shown). The output fluid plug 22 is ideally followed by air/inert gas 52 to ensure it can be pushed all the way through the concentration subsystem 14 and to avoid retaining activity in the output line. The vial 28 may also be vented with filter 56.

At this point, the isotope dispensing subsystem 12a has completed its operation and can await a new request for additional radioactivity. One 100 mCi vial 28 can support many syntheses.

Every time the radioactive isotope vial is changed, the wetted path 54 that interacts with this subsystem should be changed. This includes needles, valves (if disposable), tubing, vials, etc. In a preferred embodiment, this is achieved via disposable cassette 40 that is safe and easy to insert and remove (e.g. to avoid "spaghetti" tubing and unprotected needles). Additionally, the entire radioactive isotope dispensing subsystem 12 is designed as compact as possible to reduce fluid path lengths.

An alternative embodiment dispensing subsystem 12b is shown schematically in FIG. 5, and eliminates the need for a valve 42 in the disposable component. This is preferably achieved by lifting the needle 36 out of the fluid 28 after the desired amount of fluid has been pumped into the fluid path. The peristaltic pump 46 may then run forward and push the entire aliquot into the concentrator 14, pushing the aliquot with air drawn through the needle 36. An exemplary minimum volume may be approximately 100 uL in this embodiment so that the plug of fluid 22 does not break-up within the tubing. The needle 36 could be partially lifted (so it is out of the liquid but still inside the isotope vial 28), or could be fully lifted so it is completely out of the isotope vial 28. There is a risk that with the needle 36 out of the vial 28, additional shielding may be needed since it may be contaminated on the outside or inside with significant amounts of radioisotope. If the needle 36 remains in the vial 28, this will generate a negative pressure in the vial and it is possible that the aliquot could be pushed all the way to its destination. In such cases, a venting needle (not shown) could also be inserted through the septum of vial 28, along with a filter (not shown) on the end to avoid contamination. However, if the needle 36 is completely retracted from the vial 28, the needle will need to be pushed back through the septum each time the system 10 dispenses such that the septum forms a tight seal around the needle 36.

In one embodiment, an H-bridge driver or stepper driver is used as the actuator 58 for driving up the elevator platform 35 (see FIG. 2). This may simply be an off the shelf motor driver with a serial interface. An H-bridge driver or stepper driver may also be used to drive the peristaltic pump 46. In one embodiment, a simple H-bridge circuit is used. It should be noted that the peristaltic pump 46 may be configured to drive both forward and in reverse.

As detailed above, one embodiment of this design incorporates a valve 42 to disconnect the radioactive isotope vial from the peristaltic pump. The dispensing unit 12 could then drive air into the concentration subsystem 14. This may include 1 or 2 more DC drivers for valve actuation.

Additional sensors, along with associated circuitry, may also be incorporated to sense one or more of: the presence of a particular (e.g. BIODEX) pig 30, drawer/door state (e.g. open/closed), elevator platform 35 up or down, proper cassette engagement, shielding, etc. Many of these sensors may comprise interlock type sensors that simply use a contact switch or similar mechanism.

As shown in FIG. 4 and FIG. 5, the radioactivity sensing is preferably performed using PIN photodiodes 44. PIN photodiodes 44 are sensitive to many wavelengths of light, including the high-energy wavelengths of gamma photons. The sensing is preferably achieved with a small PIN photo diode 44 connected to an amplifier (not shown) and then an ADC (not shown). Visible light shielding (not shown) may be placed over the photodiode to shield it from this signal source. Gamma photons of 511 keV penetrate the shielding and produce pulses. The software 82 is configured such that the pulses are filtered and energy discrimination is performed via a simple comparator. The pulses are integrated by a long time constant low pass filter giving a dc value proportional to event rate. In one embodiment, two such circuits 44 are used: one directly next to the tubing and one some distance away. Software 84 may employ a subtraction algorithm to remove room background noise, and the resulting signal is used to meter the activity. The subtraction can be done in analog or digitally, so 1 or two 16-bit ADCs are used. The sampling rate can be fairly low, and averaging can be done to improve SNR. It is important that the geometry of the tubing and its proximity to the sensor 44 be reproducible.

Figure 6:
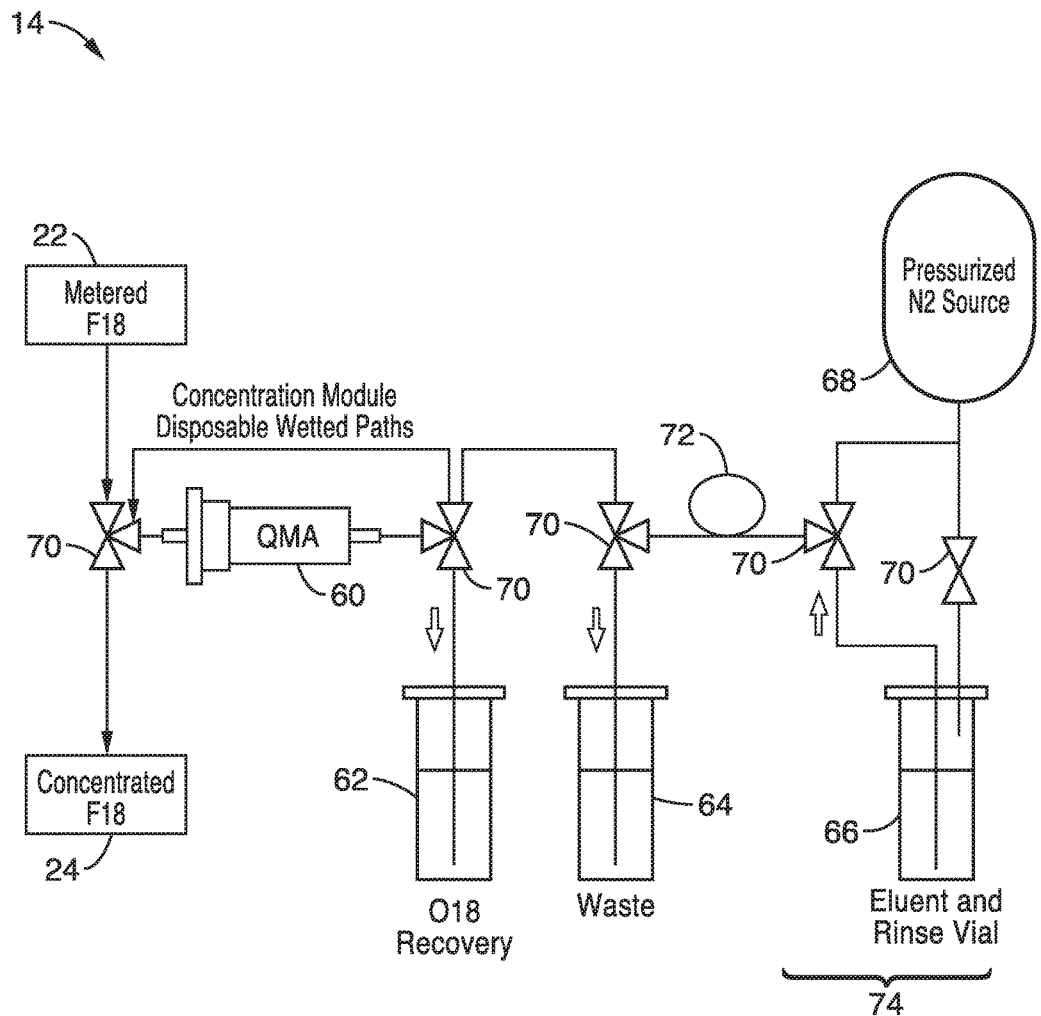
FIG. 6 shows a schematic diagram of an exemplary configuration of the concentration module shown in FIG. 1.

FIG. 6 shows a schematic diagram of an exemplary configuration of the concentration module 14. The microfluidic chip in synthesizer subsystem 16 has a limited capacity for reagent volumes (droplets of about 2-20 μL). The concentration module 14 is thus configured to reduce the volume of the radioisotope solution into this range. The key functionalities of the concentration subsystem 14 are: (a) automated concentration, (b) disposable fluidic pathways contained within a disposable cassette, (c) high trapping and release efficiencies, (d) short run time relative to the half-life of the radioisotope, and (e) achieves the desired reduction in volume. In quantitative terms, the following are exemplary targets for the concentration subsystem 14: (i) total time of under 10 minutes, (ii) final released volume of <20 μL so that most of it can be loaded to the chip, (iii) release efficiency of >80% (decay-corrected).

An amount of radioactivity (metered dose 22) from the dose dispensing subsystem 12 is directed through a cartridge 60 capable of trapping the radioactivity and sending the eluent to waste or collection vial 66. In particular, for F18 fluoride, the source of activity may be in several mLs of O18-enriched water, and thus it is necessary to reduce both the volume of the delivered droplet as well as the water content, which inhibits the reactivity of the F18 fluoride, while still maintaining the same amount of radioactivity. To do this, a "trap and release" mechanism is used. The benefit of this trap-and-release mechanism is to decrease downstream evaporation time, due to lower water content and smaller final volume. The concentration also acts as a purification step, eliminating metallic impurities that might adversely affect the synthesis.

The concentration is achieved by trapping the radioactivity onto a solid-phase extraction cartridge 60 typically filled with an ion exchange material such as quaternary methylammonium (QMA). The QMA material is positively charged and will trap the anions (e.g. F18 fluoride) from the solution, exchanging them with the anions previously bound to the QMA 60 (e.g. the anions used in preconditioning the cartridge). The user will often want to recycle the O18-enriched water after stripping it of F18 fluoride, since the water could be returned to the supplier for re-purification and reuse. Therefore, the O18 water is captured in a vial 62. The trapped F18 is then eluted off the QMA cartridge 60 by passing an eluent (liquid) 66 through the QMA 60 in the desired final volume. This concentrated F18 24 is then pushed into the synthesizer subsystem 16 to act as a reagent in the synthesizer subsystem.

In the embodiment shown in FIG. 6, the prototype uses several rotary or injector valves 70 and an injection loop 74 to first trap the radioactive isotope (F18 in the preferred embodiment for this example) onto the QMA ion exchange cartridge 60. The enriched water carrier solution passes through the cartridge 60 and is captured in a separate collection vial 62 for reuse since it can have significant value. The injection loop 74 is then used to flush the F18 off the cartridge 60 in quantized droplet volumes 72 of ~1-2 μL. Since there are two injector valves 70 for loop 74, one valve 70 has the QMA cartridge as the "loop" while the other valve 70 has a metered piece of tubing as the "loop." The metered loop can be filled from a stock of eluent 66, and the plug 72 subsequently pushed to the cartridge, allowing for a consistent volume for each eluent plug 72. This can be repeated any number of times. Eluent, stored in a vial 66, is pushed through the loop and into a waste vial 64. This procedure loads the fixed volume loop with a known quantity of eluent. The valve states are then changed and the eluent in the loop is flushed through the QMA cartridge 60 to the next subsystem. The cartridge 60 is thus washed and/or dried to remove residual solvent from the trapping step. This quantized flushing can be repeated multiple times to ensure the correct volume on the output. (Multiple steps also help to reduce the amount of residual radioactivity trapped in the fluid path.)

The functionality of the concentration subsystem 14 is largely dependent on changes in valve state. For the embodiment shown in FIG. 6, five digital high current drivers (not shown), operable via instructions/commands from software 84, may be employed for proper functioning of the valves 70. This may also depend on whether the selected valves 70 have the proper driver built in. For the concentration subsystem 14 shown in FIG. 6, a pair of Rheodyne rotary injection valves were used for the injection loop. These valves have built in drivers and can receive commands via binary encoded decimal (i.e. simple TTL values), or an available I2C interface (not shown). The I2C interface would minimize the number of wires, should multiple valves be necessary. An electronically controlled pressure regulator (e.g. SMC digital pressure regulator, not shown) may also be implemented for the driving forces.

To trigger valve state changes, liquid sensors may also be placed at different locations, e.g. the inlet to the waste vial 64 and the inlet to the loop 74. These sensors inform the system when the loop has be filled and is ready for injection. Each liquid sensor may also be coupled with an ADC for sampling the phototransistor. An alternative would be to use a comparator, and instead detect the presence of liquid with a single digital input. The advantage to using an ADC is the added algorithmic flexibility, to both debounce and filter the response and avoid miss-triggers. Note that this subsystem ideally will communicate with the isotope delivery subsystem 12 (e.g. via computer 80 and software 84). For example, after the liquid is detected at a certain point, then the delivery is complete and the delivery subsystem 12 can stop delivering gas.

Additionally, a preferred embodiment includes a radiation sensor (not shown) that is placed on the QMA cartridge 60 and is used to ensure proper trapping of the F-18 as well as proper release. Trap and release efficiency can thus be approximated in real time. Similar to the radiation sensor 44 used in the dispensing subsystem 12, a solid-state PIN diode can be used with the appropriate analog processing circuitry. Another ADC would be used for sampling the output from this sensor.

In the embodiment shown in FIG. 6, the motive force for loop 74 is generated from a regulated source 68 (e.g. N2). It is appreciated that use of an additional pump (similar to peristaltic pump 46) may be implemented, or the subsystems 12, 14 configured such that the fluid is driven by motive force from the previous subsystem 12, to reduce the infrastructure requirements for an N2 source.

In a preferred embodiment, all wetted paths in the concentration subsystem 14 are disposable, compact, and in cassette form. Furthermore, all wetted paths and vials (except the initial eluent vial 66) are hot and should be shielded. Preferably, disposable valves 70 are used to actuate these steps. In an alternative embodiment (not shown) the concentration subsystem 14 may be integrated with the synthesizer subsystem 16 to reduce shielding, and the wetting paths of both subsystems could be combined to reduce costs. In a preferred embodiment, disposable valves are used to actuate the above-detailed steps. Alternatively, non-disposable valves could be used. In a preferred embodiment, all materials are solvent-resistant.

Figure 7:
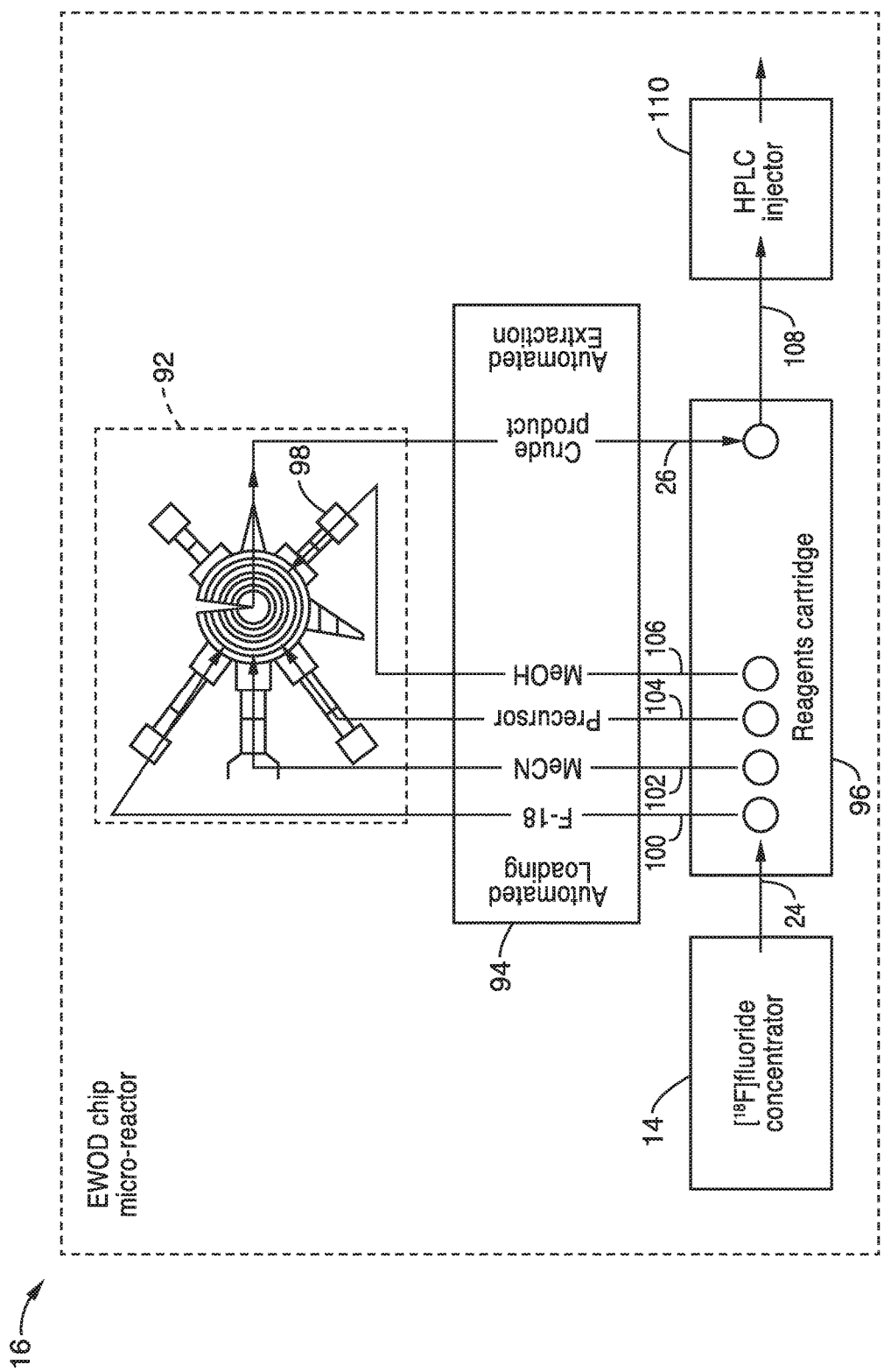
FIG. 7 shows a schematic diagram of an exemplary synthesizer subsystem shown in FIG. 1.

Referring now to FIG. 7, the synthesizer subsystem 16 is generally configured to deliver reagents (including concentrated radioactive isotope 24 from the concentrator subsystem 14) to the chip 92, where the radiolabeled molecule will be produced. The synthesizer subsystem 16 generally comprises five main components: (1) concentrated radioactive isotope 24 from the concentration subsystem 14, 2) the EWOD (electrowetting on dielectrics) chip 92 and its holder (i.e. the "chip cassette," which may be in the configuration of chip cassette 90 shown in FIG.), 3) the reagents cartridge 96 and its holder (i.e. the "reagent cassette," (not shown) which may be separable from or integrated with chip cassette 90), 4) the output line 108 to support HPLC purification 5) and a disposable cassette (not shown) for trap and release cartridge purification (vials, cartridge, valves, etc.). The above components may be controlled by an electronic control system or systems, which may include computer 80 shown in FIG. 1. Synthesis protocols are chosen by the user via an integrated software graphical user interface, which may be a component or module of software 84. The order of reagents delivered to the chip is controlled by these protocols, as are reaction unit operations such as heating, mixing, etc.

FIG. 7 schematically illustrates the fluid to chip interface 94 that supports automatic loading of reagents (F-18 (100), MeCN (102), precursor (104), MeOH (106)) from the reagents cartridge to the fluidic manifold/reactor 98 on chip 92, which is used to control metered fluid flow between the reagents and the chip. The fluid to chip interface 94 also includes automated extraction from fluidic manifold 98 of the crude product 26 that is the fed through HPLC injector 110.

Figure 11:
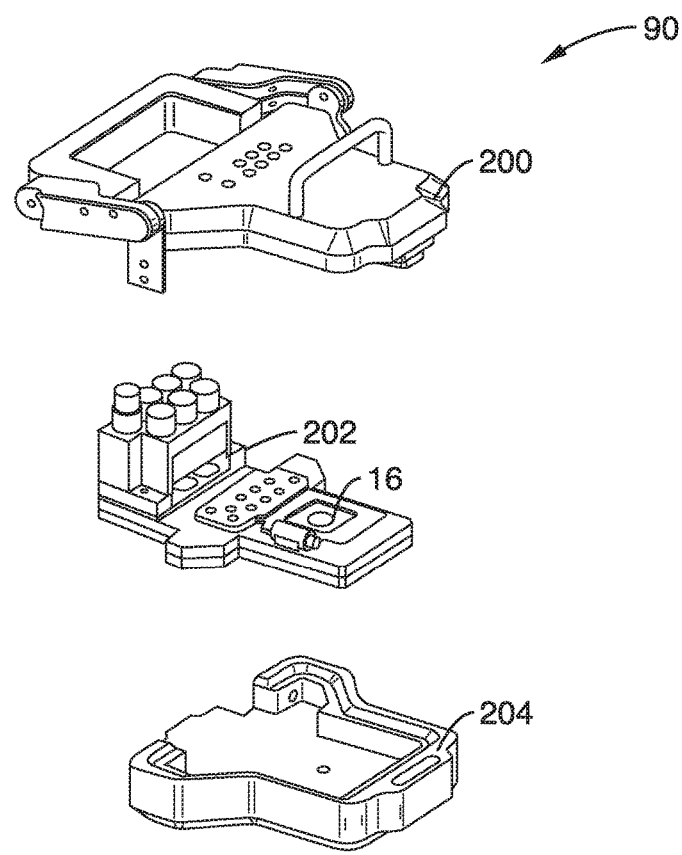
FIG. 11 shows an exploded perspective view of a chip cassette in accordance with the present description.

As illustrated in FIG. 7, the concentrator subsystem 14 may be "on chip" with the synthesizer subsystem 16, and fully contained within the chip cassette 90 (shown in greater detail in FIG. 11. The chip cassette 90 and reagent cassette (holding reagent cartridge 96) may be separable or integrated into a single reagent-chip cassette, which may also contain the concentrator subsystem 14. Alternatively, multiple chips may be used and hooked together with fluidic connections, such as a manifold or cartridge or tubing.

In a preferred embodiment, all wetted paths are disposable and any wetted paths that are radioactive are contained within shielding that can attenuate beta and gamma rays. Any wetted paths that are not radioactive are contained outside shielding. Furthermore, the shielding that holds the reagent-chip cassette (e.g. cassette 90) and concentrator subsystem 14 can be removed from the main system 10 and placed away from the main system 10 to allow the radioactivity to safely decay.

The reagent-chip-concentrator cassette/cassettes is/are preferably made from solvent-resistant materials. The reagents (100-106) may be held in sealed vials (see reservoirs 152 in FIG. 9) and delivered "on-demand" (when the synthesis protocol calls for them) by breaching the seal. These seals generally comprise a septum cap, such as cap 122 shown in FIG. 8. In a preferred embodiment, reagents are metered out, so that one vial can provide multiple batches of reagent to participate in different stages of the reaction.

Figure 8:
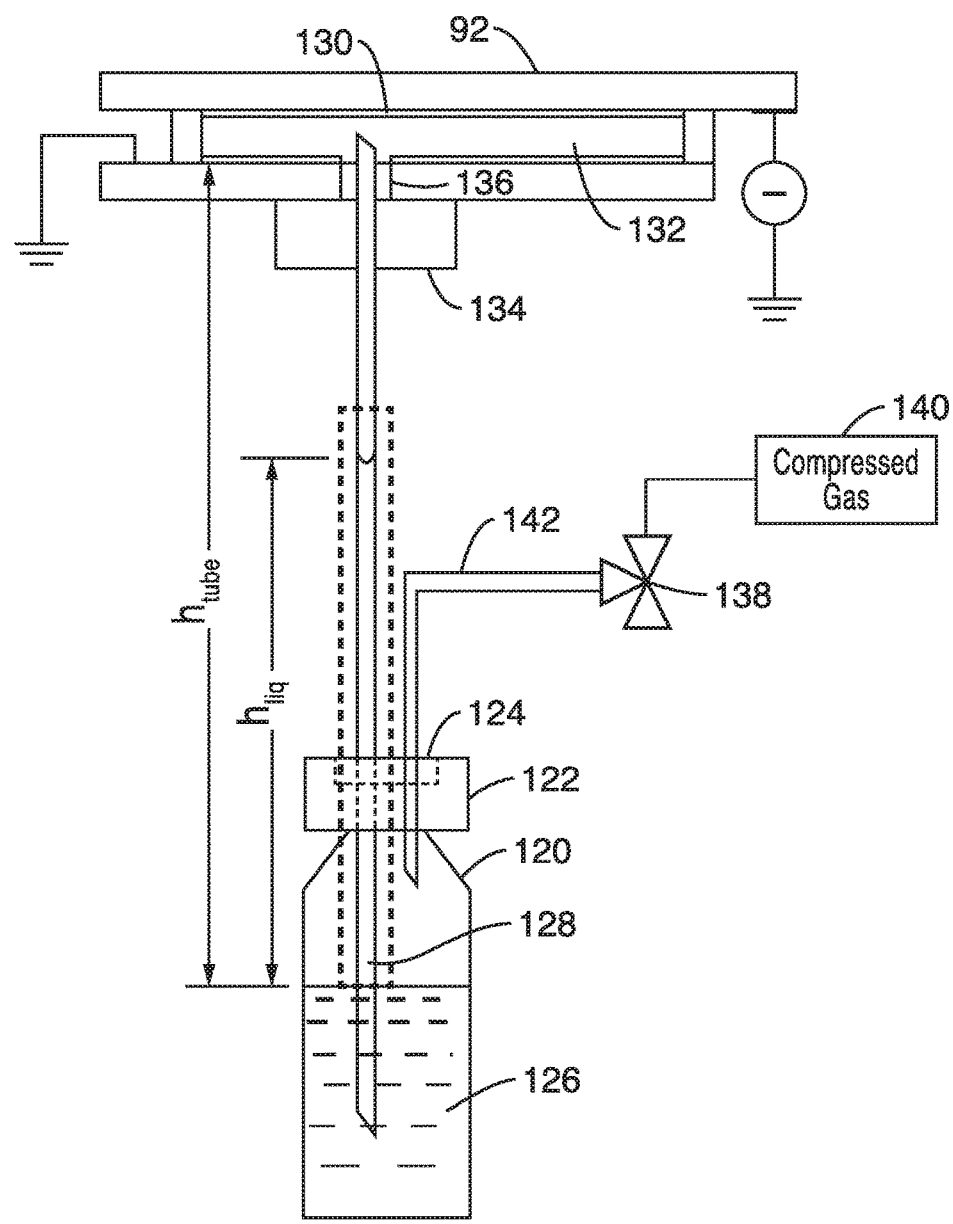
FIG. 8 illustrates a schematic view of a first embodiment of a synthesizer subsystem using gravity and pressure delivery.

FIG. 8 illustrates a schematic view of a first embodiment of a synthesizer subsystem 16a using gravity and pressure delivery. In this embodiment, liquid 126 is delivered to the EWOD chip 92 from sealed reservoirs through vertical tubing, using pressurized gas 140 to pump liquid towards the chip 92. EWOD force is used to retain the desired amount of liquid on the chip 92 and gravity to remove excess liquid from the chip back into the reservoir or vial 120.

On-demand delivery of μL volumes from 100 s of μL are accomplished as follows: reservoirs 120 in the form of reagent vials having caps 122 with septums 124 are placed vertically below the EWOD chip 92. A vertical needle 128 ("liquid needle") is dipped into the reservoir 120 and leads up through gasket 134 to the corresponding inlet hole 136 on the bottom substrate 135 of the EWOD chip 92. A separate shorter needle 142 ("gas needle") allows introduction of compressed gas 140 into the vial. On demand, the vial 120 is gently pressurized (controlled through a gas valve 138 and pressure regulator (not shown)) in order to send the liquid 126 up towards the EWOD chip 92 against gravity. Short pulses (e.g. 100 ms) of low pressure (~0.5-10 kPa) are used to pump liquid from vials 120 into the chip 92.

At the loading site 132 on the chip 92, the activated EWOD electrode 130 provides a retention force to hold the liquid 126 in the chip 92, as well as detects impedance change as the liquid enters the gap. Once sufficient liquid has been detected at the loading site 132, the pressure is turned off (e.g. by switching from the pressure source to vent using a pneumatic valve), so that gravity pulls back the liquid column 126 back into the reservoir 120. The liquid retained using EWOD at the loading site 132 stays on the chip 92, while the rest of the liquid is pulled back into the reservoir 120.

After the loaded droplet is moved off the loading site (e.g. to the manifold/reactor 98) by EWOD, the same process can be repeated to load multiple droplets from one or more reservoirs. This technique works with most organic and aqueous liquids used in radiochemistry, providing an accuracy of ±10% for ~2 uL droplet volume delivered to the chip 92. At the end of the synthesis, one of the lines (see FIG. 7) will be used for removal of the crude product 26 at the end of the synthesis, by applying vacuum to an empty septum capped vial. The liquid handling needed for the concentration subsystem 14 and interface to purification (e.g. HPLC) module 18 can potentially be done with a gas-based mechanism as well, but this is not necessary.

Figure 9:
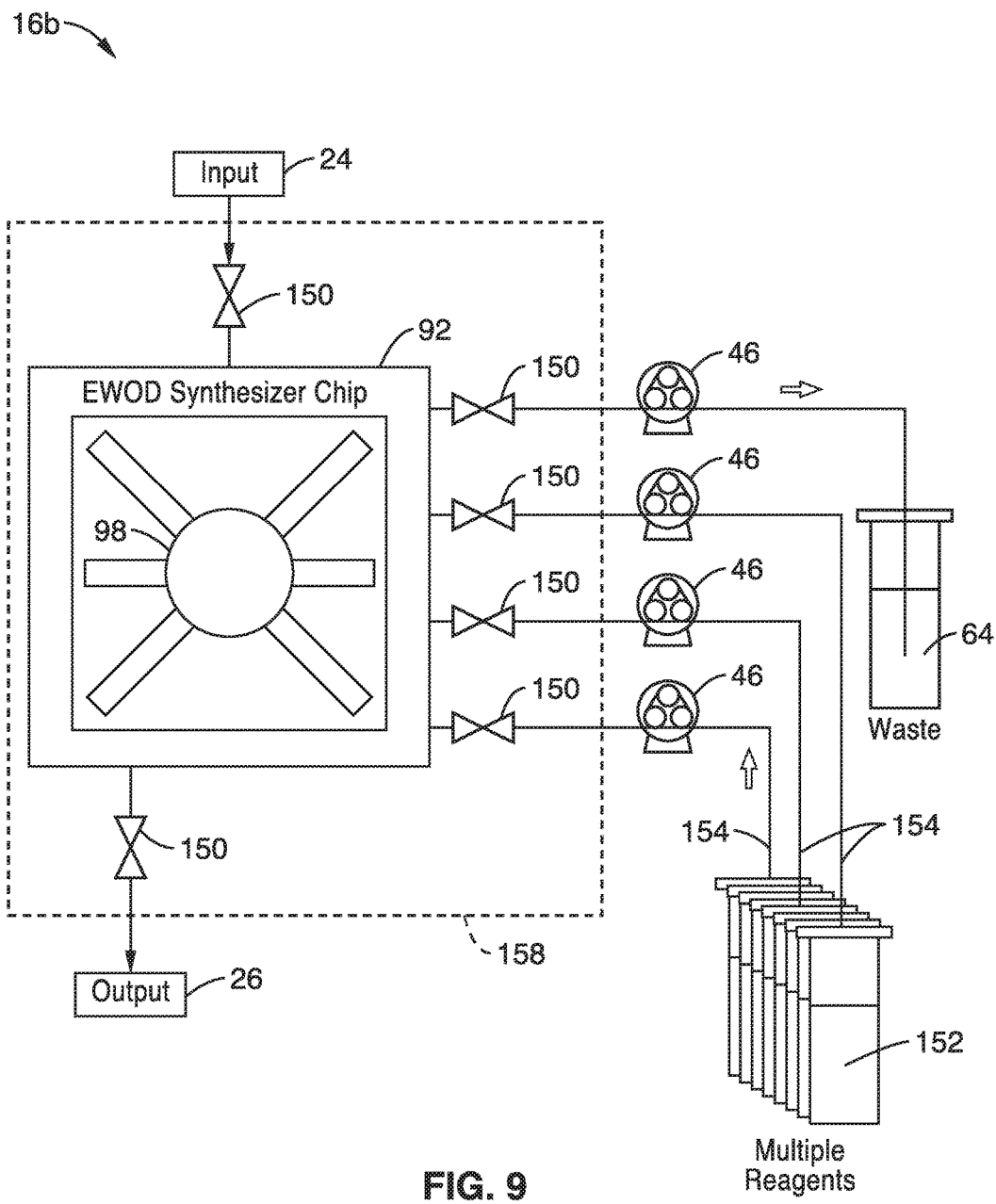
FIG. 9 illustrates a schematic view of a second embodiment of a synthesizer subsystem using peristaltic pumping on molded fluid pathways.
Figure 10:
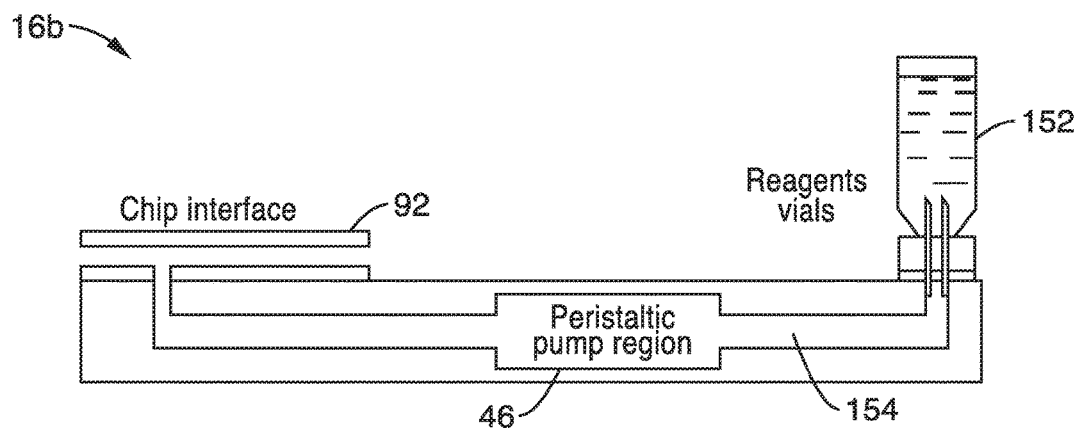
FIG. 10 shows a side view of the synthesizer subsystem of FIG. 9.

FIG. 9 illustrates a schematic view of a second embodiment of a synthesizer subsystem 16b using peristaltic pumping on molded fluid pathways to create a simple and cheap reagent delivery. FIG. 10 shows a side view of the synthesizer subsystem 16b of FIG. 9. As shown in FIG. 9, reagent from multiple reagent reservoirs 152 is driven by peristaltic action via pumps 46 through molded fluid pathways or lines 154 to the chip 92 and reactor/manifold 98. Volumetric control can be achieved by appropriate choice of channel 154 diameter and peristaltic pump 46. Waste may also be taken from reactor 98 via a pump 46 to waste vial 64. A plurality of pinch-off mechanisms 150 may be employed to contain all reagent 152 and activity (e.g. input 24 and output 26) from backing up out of the shielding 158. After synthesis is completed, the chip 92 and shielding 158 assembly will be removed and stored to decay. All wetted paths from reagents 152 and pathways 154 may also be contained in disposable cassettes. A ribbon cable (not shown) for carrying actuation voltages to the EWOD chip 92 may jog through the shielding 158 to avoid unwanted shine coming from the EWOD chip 92.

In one exemplary embodiment, actuation of EWOD chip 92 electrodes may be achieved via a 50 conductor ribbon cable (not shown) with standard 50 mil spacing for carrying actuation voltages to the EWOD chip 92. The chip contact pads (e.g. electrode 130 of FIG. 8) interface with a corresponding array (2×20 pins on a 1.27×1.27 mm grid) of spring-loaded contact pins ("pogo-pins") on a PCB board (not shown), which interfaces to the electronics through a ribbon cable.

Additionally, a feedback-controlled heating system (not shown) may be used with temperature sensing through a thermocouple and configured for heating occurring through a heat transfer rod (not shown). The rod is integrated into the shielding 158 around the chip 92. The rod may be made from tungsten or lead to provide shielding, and may incorporate a thin layer of thermal insulation around the rod. It may be desirable to have a complex shape through the shielding to avoid shine via the insulating material (e.g. a cylinder of two different diameters). Heating (and cooling) will be provided by the fixed platform. The heat transfer rod in the chip shielding will contact this temperature actuator at the time of shielded chip installation. The heating rod may have a circular shape (12 mm diam.) at the end in contact with the chip 92 inside the shielding 158.

FIG. 11 shows an exploded perspective of chip cassette 90 in accordance with the present description. Chip cassette 90 shows a disposable fluidic manifold 202 configured to be disposed between a tungsten carrier top 200 and tungsten carrier bottom 204. The disposable fluidic manifold 202 is shown coupled to synthesizer module 16, however it is appreciated that concentration module 14 may also be incorporated within the cassette 90. The tungsten carrier top 200 and tungsten carrier bottom 204 may be configured to house any of the disposable cassettes detailed herein.

With respect to the HPLC and cartridge formulation and purification module/subsystem 18, immediately after on-chip synthesis, the desired PET tracer (raw product 26) resides in a mixture of different unwanted solvents, side products, and unused precursor that must be removed. After the PET tracer is synthesized on chip it will be transferred off of the chip to one of the 2 purification methods: (1) Cartridge Purification and (2) HPLC purification. The pathway may be selected by a valve, or, the chip manifold may be specifically tailored for certain types of probes and only contain the pathway to the corresponding purification method. For both cartridge purification and HPLC purification, the final product is to be formulated into a solvent and volume appropriate to animal or human injection.

After purification, the purified fraction is often not suitable for injection and must therefore be diluted in or replaced by saline buffer of the appropriate salt concentration and pH. This "formulation" requires a separate module. Heating in an evacuated container evaporates the solvent present in the purified fraction.

Once most of the solvent is removed, the purified product is re-dissolved in a saline buffer having the appropriate pH and salt concentration for injection.

Another method of performing the solvent exchange is to use a cartridge. The sample is passed through the cartridge and the species of interest remains trapped on the resin. The species of interest is then released by an eluent. Ideally, this eluent is safe for injection directly. Sometimes, e.g. if the eluent is ethanol, the eluent must be diluted in saline prior to injection.

The entirety of the purified product can be sent to a shielded collection vial or syringe (or other apparatus/location). In another embodiment, a portion of the purified product is sent to an integrated quality control system that analyzes the contents of the product for its purity, composition, and sterility.

In another embodiment, purification can be performed on-chip.

In the preferred embodiments detailed above, the system 10 is described for use with the synthesis of radiochemical PET tracers, but it is appreciated that system 10 can be configured for use with other radioactive material processing such as generation of SPECT tracers, radiotherapeutic or theranostic agents, etc. Furthermore, the system 10 can also be used for other general chemistry and biological manipulations.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that the present disclosure encompasses multiple embodiments which include, but are not limited to, the following:

1. A self-shielded, bench-top radio chemistry system, comprising: a radioactive isotope dispensing module configured to draw an isotope out of a reservoir and dispense a metered dose of said isotope; a concentration module configured to receive the metered dose from the dispensing module and concentrate the metered dose into a droplet amount of isotope; and a synthesizer module configured to receive the droplet amount of isotope from the concentration module and deliver the droplet amount of isotope along with one or more reagents to a microfluidic chip to produce a radiolabeled molecule.

2. The system of any preceding embodiment, wherein the dispensing module, concentration module and synthesizer module are integrated and automated so that fluidic, electrical, and mechanical connections run from each module to the next without substantial loss of fluid or radioactivity.

3. A system as recited in claim provided in any of the previous embodiments: wherein each of the dispensing module, concentration module and synthesizer module are connected in fluid communication via one or more wetted paths; wherein the one or more wetted paths are exposed to said isotope; and wherein portions of the one or more of the dispensing module, concentration module and synthesizer module corresponding to said one or more wetted paths are disposed in a shielded, disposable cassette.

4. The system of any preceding embodiment: wherein the dispensing module comprises a sensor for measuring radioactivity at a location within the dispensing module; and wherein the dispensing module is configured to dispense said metered doses as a function of radioactivity measured at the location.

5. The system of any preceding embodiment, wherein the dispensing module comprises a pumping mechanism to draw the isotope from the reservoir and generate the metered dose.

6. The system of any preceding embodiment, the dispensing module further comprising: a needle disposed within the dispensing module; and an actuator coupled to either the needle or the reservoir such that operation of the actuator automatically draws the needle into or out of the reservoir.

7. The system of any preceding embodiment: wherein the concentration module comprises a concentrator cartridge; and wherein the metered dose is delivered through the cartridge along with an eluent to generate said droplet amount of isotope.

8. The system of any preceding embodiment, wherein the synthesizer module comprises a micro-fluidic manifold configured to deliver the droplet amount of isotope and one or more reagents in individual channels to the microfluidic chip.

9. The system of any preceding embodiment, wherein at least portions of two or more of the dispensing module, concentration module and synthesizer module are integrated on to a single disposable cassette.

10. The system of any preceding embodiment, further comprising: a purification and formulation module configured to collect unpurified product from the synthesizer module and generate a purified product.

11. A method for generating a radiolabled molecule, comprising: drawing a radioactive isotope out of a reservoir and dispensing a metered dose of said isotope; receiving the metered dose and concentrating the metered dose into a droplet amount of isotope; and delivering the droplet amount of isotope along with one or more reagents to a microfluidic chip to produce a radiolabled molecule.

12. A method as provided in any of the previous embodiments, wherein the dispensing, concentration and delivery of the isotope to the microfluidic chip are automatically performed within a shielded apparatus without substantial loss of fluid or radioactivity.

13. The method of any preceding embodiment: wherein the isotope is dispensed, concentrated and delivered to the microfluidic chip within the apparatus along one or more wetted paths that expose to said isotope; and
wherein portions of the apparatus corresponding to said one or more wetted paths are disposed in a shielded, disposable cassette.

14. The method of any preceding embodiment, further comprising: measuring radioactivity at a location within the apparatus corresponding to the dispensing of the metered dose of said isotope; and dispensing said metered doses as a function of radioactivity measured at the location.

15. The method of any preceding embodiment, wherein peristaltic pump is used to draw the isotope from the reservoir and generate the metered dose.

16. The method of any preceding embodiment, wherein the apparatus comprises a needle disposed within the apparatus, the method further comprising: automatically drawing the needle into or out of the reservoir 17. The method of any preceding embodiment: wherein concentrating the metered dose comprises delivering the metered dose and an eluent through a cartridge to generate said droplet amount of isotope.

18. The method of any preceding embodiment, wherein the droplet amount of isotope and one or more reagents are delivered in individual channels of a micro-fluidic manifold to the microfluidic chip.

19. The method of any preceding embodiment the method further comprising: removing the cassette containing the wetted paths while the reservoir remains disposed within the apparatus; installing a second, unused cassette; drawing radioactive isotope out of the reservoir and dispensing a second metered dose of said isotope; receiving the second metered dose and concentrating the second metered dose into a second droplet amount of isotope; and delivering the second droplet amount of isotope along with one or more reagents to a microfluidic chip to produce a second radiolabled molecule.

20. The method of any preceding embodiment, wherein the microfluidic chip comprises an EWOD chip.

21. A fully-integrated chip-based chemical synthesizer, comprising: a dispensing module configured to draw an agent out of a reservoir and dispense a metered dose of said agent; and a synthesizer module configured to receive the metered dose of agent from the concentration module and deliver the droplet amount of agent along with one or more reagents to a microfluidic chip to produce a labeled molecule.

22. The synthesizer of any preceding embodiment, further comprising: a concentration module configured to receive the metered dose from the dispensing module and concentrate the metered dose into a droplet amount of agent for deliver to the synthesizer module.

23. The synthesizer of any preceding embodiment: wherein the agent comprises an isotope; and wherein the dispensing module, concentration module and synthesizer module are integrated and automated so that fluidic, electrical, and mechanical connections run from each module to the next without substantial loss of fluid or radioactivity.

24. The synthesizer of any preceding embodiment: wherein each of the dispensing module, concentration module and synthesizer module are connected in fluid communication via one or more wetted paths; wherein the one or more wetted paths are exposed to said isotope; and wherein portions of the one or more of the dispensing module, concentration module and synthesizer module corresponding to said one or more wetted paths are disposed in a shielded, disposable cassette.

25. The synthesizer of any preceding embodiment, wherein the dispensing module comprises a sensor for measuring radioactivity at a location within the wherein the dispensing module; and wherein the dispensing module is configured to dispense said metered doses as a function of radioactivity measured at the location.

26. The synthesizer of any preceding embodiment, wherein the dispensing module comprises a pump to draw the isotope from the reservoir and generate the metered dose.

27. The synthesizer of any preceding embodiment, the dispensing module further comprising: a needle disposed within the dispensing module; and an actuator coupled to either the needle or the reservoir such that operation of the actuator automatically draws the needle into or out of the reservoir.

28. The synthesizer of any preceding embodiment: wherein the concentration module comprises a concentrator cartridge; and wherein the metered dose is delivered through the cartridge along with an eluent to generate said droplet amount of isotope.

29. The synthesizer of any preceding embodiment, wherein the synthesizer module comprises a micro-fluidic manifold configured to deliver the droplet amount of isotope and one or more reagents in individual channels to the microfluidic chip.

30. The synthesizer of any preceding embodiment, wherein at least portions of two or more of the dispensing module, concentration module and synthesizer module are integrated on to a single disposable cassette.

31. The synthesizer of any preceding embodiment, further comprising: a purification and formulation module configured to collect unpurified product from the synthesizer module and generate a purified product.

32. The synthesizer of any preceding embodiment, wherein the microfluidic chip comprises an EWOD chip.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A self-shielded, bench-top radio chemistry system for use without the need of a hot cell, comprising:
    a radioactive isotope dispensing module comprising fluid line, mechanical pump, and radiation sensor, the dispensing module configured to draw an isotope out of a reservoir and dispense a metered dose of said isotope;
    a concentration module comprising a solid-phase extraction cartridge and configured to receive the metered dose from the dispensing module and concentrate the metered dose into a droplet amount of isotope;
    a synthesizer module comprising a disposable chip cassette holding a microfluidic chip and a reagent cartridge configured to receive the droplet amount of isotope from the concentration module and deliver the droplet amount of isotope along with one or more reagents to the microfluidic chip to produce a radiolabeled molecule;
    a computer control system operably coupled to the radioactive isotope dispensing module, concentration module, and synthesizer module to automatically control their respective operations;
    a plurality of shielded carriers configured to hold the disposable chip cassette therein and openable to remove the disposable chip cassette therefrom;
    wherein each of the dispensing module, concentration module and synthesizer module are connected in fluid communication via one or more wetted paths;
    wherein the one or more wetted paths are exposed to said isotope; and
    wherein the microfluidic chip and portions of the one or more of the dispensing module, concentration module and synthesizer module corresponding to said one or more wetted paths are disposed in the disposable chip cassette contained in one of the plurality of shielded carriers disposed inside the bench-top radio chemistry system, wherein the shielded carrier containing the disposable chip cassette is removable from the bench-top radio chemistry system.

2. A system as recited in claim 1, wherein the dispensing module, concentration module and synthesizer module are integrated and automated using a program executed on the computer control system so that fluidic, electrical, and mechanical connections run from each module to the next without substantial loss of fluid or radioactivity.

3. A system as recited in claim 1:
    wherein the computer control system receives information from the radiation sensor and controls the dispensing module to dispense said metered doses as a function of radioactivity measured at the location.

4. A system as recited in claim 1, wherein the mechanical pump comprises a peristaltic pump.

5. A system as recited in claim 1, the dispensing module further comprising:
a needle disposed within the dispensing module; and
an actuator coupled to either the needle or the reservoir such that operation of the actuator automatically draws the needle into or out of the reservoir.

6. A system as recited in claim 1, wherein the synthesizer module comprises a disposable micro-fluidic manifold configured to deliver the droplet amount of isotope and one or more reagents in individual channels to the microfluidic chip.

7. A system as recited in claim 1, wherein one or more of the dispensing module and concentration module are integrated on the disposable chip cassette.

8. A system as recited in claim 1, further comprising:
a purification and formulation module configured to collect unpurified product from the synthesizer module and generate a purified product.

9. A method for generating a radiolabled molecule without the need of a hot cell, comprising:
providing a self-shielded, bench-top radio chemistry system having a computer controlled radioactive isotope dispensing module, a concentration module, and a synthesizer module comprising a disposable chip cassette holding a microfluidic chip and a reagent cartridge, wherein the isotope is dispensed, concentrated and delivered to the microfluidic chip within one or more wetted paths of the radioactive isotope dispensing module, the concentration module, and the synthesizer module that are exposed to said isotope, and wherein the microfluidic chip and portions of the one or more wetted paths are disposed in the disposable chip cassette contained in a first shielded carrier;
automatically drawing a radioactive isotope out of a reservoir contained in the radioactive isotope dispensing module with a mechanical pump and dispensing a metered dose of said isotope;
automatically receiving the metered dose in the concentration module comprising a solid-phase extraction cartridge and concentrating the metered dose into a droplet amount of isotope;
automatically delivering the droplet amount of isotope along with one or more reagents from the reagent cartridge to the microfluidic chip in the disposable chip cassette to produce a radiolabeled molecule;
removing the first shielded carrier containing the disposable chip cassette from the bench-top radio chemistry system;
loading a second shielded carrier containing a second disposable chip cassette into the bench-top radio chemistry system.

10. A method as recited in claim 9, further comprising:
measuring radioactivity at a location within the dispensing module with a sensor contained therein; and
dispensing said metered doses as a function of radioactivity measured at the location.

11. A method as recited in claim 9, wherein a peristaltic pump is used to draw the isotope from the reservoir and generate the metered dose.

12. A method as recited in claim 9, wherein the apparatus comprises a needle disposed within the dispensing module, the method further comprising:
automatically drawing the needle into or out of the reservoir.

13. A method as recited in claim 9:
wherein concentrating the metered dose comprises delivering the metered dose and an eluent through a cartridge in the concentration module to generate said droplet amount of isotope.

14. A method as recited in claim 9, wherein the droplet amount of isotope and one or more reagents are delivered in individual channels of a micro-fluidic manifold to the microfluidic chip.

15. A method as recited in claim 9, the method further comprising:
removing the first shielded carrier containing the disposable chip cassette containing the wetted paths while the reservoir remains disposed within the bench-top radio chemistry system;
installing the second, unused disposable chip cassette disposed inside the second shielded carrier in the bench-top radio chemistry system;
automatically drawing radioactive isotope out of the reservoir contained in the radioactive isotope dispensing module and dispensing a second metered dose of said isotope;
automatically receiving the second metered dose in the concentration module and concentrating the second metered dose into a second droplet amount of isotope; and
automatically delivering the second droplet amount of isotope along with one or more reagents from the reagent cartridge to a microfluidic chip of the second disposable chip cassette to produce a second radiolabled molecule.

16. A method as recited in claim 9, wherein the microfluidic chip comprises an EWOD chip.

17. A self-shielded, bench-top radio chemistry system for use without the need of a hot cell, comprising:
a radioactive isotope dispensing module comprising fluid line and a mechanical pump, the dispensing module configured to draw an isotope out of a reservoir and dispense a metered dose of said isotope;
a plurality of shielded carriers;
a disposable chip cassette holding a microfluidic chip and a reagent cartridge disposed in one of the plurality of shielded carriers, the chip cassette comprising a concentration module configured to receive the metered dose from the dispensing module and concentrate the metered dose into a droplet amount of isotope and a synthesizer module configured to receive the droplet amount of isotope from the concentration module and deliver the droplet amount of isotope along with one or more reagents to the microfluidic chip to produce a radiolabeled molecule; and
a computer control system operably coupled to the radioactive isotope dispensing module, concentration module, and synthesizer module to automatically control their respective operations, wherein the shielded carrier containing the disposable chip cassette is removeable and replaceable with another shielded carrier containing another disposable chip cassette.

18. The system of claim 17, wherein the dispensing module is disposed inside a separate dispensing cassette.

19. The system of claim 18, wherein the separate dispensing cassette is contained in separate shielded carrier.

* * * * *